(12) United States Patent
Bazan et al.

(10) Patent No.: US 7,442,447 B2
(45) Date of Patent: Oct. 28, 2008

(54) BINAPHTHOL BASED CHROMOPHORES FOR THE FABRICATION OF BLUE ORGANIC LIGHT EMITTING DIODES

(75) Inventors: Guillermo C. Bazan, Santa Barbara, CA (US); Hadjar Benmansour, Goleta, CA (US); Yoshiharu Sato, Sagamihara (JP); Takeshi Shioya, Yokohama (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/759,505

(22) Filed: Jan. 16, 2004

(65) Prior Publication Data

US 2004/0151945 A1    Aug. 5, 2004

Related U.S. Application Data

(63) Continuation-in-part of application No. 10/346,667, filed on Jan. 17, 2003, now abandoned.

(51) Int. Cl.
*H01J 1/62* (2006.01)
*C09K 11/06* (2006.01)

(52) U.S. Cl. ............... 428/690; 428/917; 313/504; 313/506

(58) Field of Classification Search ............... 257/40; 313/503, 504, 506; 428/690, 917
See application file for complete search history.

(56) References Cited

U.S. PATENT DOCUMENTS

| | | | |
|---|---|---|---|
| 5,189,136 A | | 2/1993 | Wudl et al. |
| 5,480,217 A | | 1/1996 | Ohtsu |
| 5,798,170 A | | 8/1998 | Gang et al. |
| 5,929,239 A | * | 7/1999 | Langhals et al. ............ 546/37 |
| 5,985,417 A | * | 11/1999 | Shi et al. ............ 428/195.1 |
| 6,582,837 B1 | * | 6/2003 | Toguchi et al. ............ 428/690 |
| 6,656,608 B1 | * | 12/2003 | Kita et al. ............ 428/690 |
| 2002/0015859 A1 | | 2/2002 | Watanabe et al. | |

FOREIGN PATENT DOCUMENTS

| | | |
|---|---|---|
| EP | 0797375 A2 | 9/1997 |
| JP | A-57-51781 | 3/1982 |
| JP | A-59-194393 | 11/1984 |
| JP | A-63-295695 | 12/1988 |
| JP | A-1-245087 | 9/1989 |
| JP | A-1-256584 | 10/1989 |
| JP | A-2-216791 | 8/1990 |
| JP | A-2-222484 | 9/1990 |
| JP | A-3-33183 | 2/1991 |
| JP | A-4-145192 | 5/1992 |

(Continued)

OTHER PUBLICATIONS

PCT Search report dated Jun. 8, 2004.

(Continued)

*Primary Examiner*—Bruce H. Hess
*Assistant Examiner*—Camie S Thompson
(74) *Attorney, Agent, or Firm*—Berliner & Associates

(57) ABSTRACT

A blue electroluminescent material based on a binaphtyl compound of the general formula (I). Particular embodiments having the general formula have good solubilities in common organic solvents, resist crystallization and can be sublimed in a device fabrication process. These properties enable the fabrication of organic electroluminescent devices.

4 Claims, 4 Drawing Sheets

FOREIGN PATENT DOCUMENTS

| | | |
|---|---|---|
| JP | A-4-308688 | 10/1992 |
| JP | A-4-335087 | 11/1992 |
| JP | 4-70773 | 3/1993 |
| JP | A-5-159882 | 6/1993 |
| JP | A-5-198378 | 8/1993 |
| JP | A-5-198380 | 8/1993 |
| JP | A-5-214332 | 8/1993 |
| JP | A-5-A198377 | 8/1993 |
| JP | A-5-234681 | 9/1993 |
| JP | A-172751 | 6/1994 |
| JP | A-6-322362 | 11/1994 |
| JP | 10255984 | 9/1998 |
| JP | A-11-273867 | 10/1999 |
| JP | A-2000-21572 | 1/2000 |
| WO | WO9804610 | 2/1998 |

OTHER PUBLICATIONS

Applied Physics Letters- vol. 75, No. 24, Dec. 13, 1999—Efficient light-emitting iodes based on a binaphthalene-containing polymer. Jen, Alex et al.

Macromol. Chem Phys. 2002, 203, No. 1—A Binaphthyl-Bithiophene Copolymer for LightEmitting Devices. Liu, Yungi et al.

Macromol Chem. Phys. 2002, 203, No. 1; A Binaphtyhyl-Bithiophene Copolymer for Light-Emitting Devices; Yungi Liu, et al.

1999 American Institute of Physics; vol. 75, No. 24, Dec. 13, 1999; Efficient light-emitting diodes based on a binaphthalene-containing polymer; Alex K-Y Jen, et al.

Becker, H. et al. "Soluble PPVs with Enhanced Performance—A Mechanistic Approach." *Advanced Materials*, 12(1):42-48 (2000).

Braun, D. et al. "Electroluminescence and electrical transport in poly(3-octylthiophene) diodes." *J. Appl. Phys.*, 72(2):564-568 (1992).

Burroughs, J.H. et al. "Light-emitting diodes based on conjugated polymers," *NATURE*, 347:539-541 (1990).

Cao, Y. et al. "Solution-cast films of polyaniline: Optical-quality transparent electrodes." *Appl. Phys. Lett.*, 60(22):2711-2713 (1992).

Hung, L.S. et al. "Enhanced electron injection in organic electroluminescence devices using an Al/LiF electrode." *Appl. Phys. Lett.*, 70(2):152-154 (1997).

Ostrowski, J.C. et al. "Glass-Forming Binaphthyl Chromophores." *Chem. Eur. J.*, 7(20):4500-4511 (2001).

Parker, I.D. et al, "Lifetime and degradation effects in polymer light-emitting diodes," *Journal of Applied Physics* 85(4):2441-2447 (1999).

Salbeck, J. et al. "Low molecular organic glasses for blue electroluminescence," *Synthetic Metals*, 91:209-215 (1997).

Shirota, Y. et al. "Starburst molecules based on π-electron systems as materials for organic electroluminescent devices," *Journal of Luminescence*, 72-74:985-991 (1997).

Shirota, Y. "Organic materials for electronic and optoelectronic devices," *J. Mater. Chem.*, 10:1-25 (2000).

Van Slyke, S.A. et al. "Organic electroluminescent devices with improved stability." *Appl. Phys. Lett.*, 69(15):2160-2162 (1996).

Tanaka, H. et al. "Novel hole-transporting materials based on triphenylamine for organic eelctroluminescent devices." *Chem. Commun.*, 2175-2176 (1996).

Wakimoto, T. et al. "Organic EL Cells Using Alkaline Metal Compounds as Electron Injection Materials." *IEEE Transactions on Electron Devices*, 44(8);1245-1248 (1997).

Yang, Y. et al. "Polyaniline as a transparent electrode for polymer light-emitting diodes: Lower operating voltage and higher efficiency." *Appl. Phys. Lett.*, 64(10):1245-1248 (1994).

* cited by examiner

BINAPHTHOL BASED CHROMOPHORES FOR THE FABRICATION OF BLUE ORGANIC LIGHT EMITTING DIODES

CROSS REFERENCE TO RELATED APPLICATION

This application is a continuation-in-part of Ser. No. 10/346,667 filed on Jan. 17, 2003 now abandoned.

BACKGROUND OF THE INVENTION

Description of the Related Art

Semiconducting (conjugated) polymers, oligomers and small molecules have been studied as electroluminescent materials for use in light emitting displays since the early 1990s. Such emissive polymer displays offer a number of advantages, including high brightness at low operating voltage, low weight, thin profile and low power consumption over conventional display elements such as incandescent lamps and liquid crystal displays.

The requirements of the electroluminescent layer for use in high efficiency, stable light emitting devices include the following:

A. High Photoluminescence ("PL") Efficiency
In an efficient luminescent medium, radiative recombination is favored over non-radiative recombination. PL efficiencies in excess of 10% are preferred; PL efficiencies in excess of 25% are still more preferred; and PL efficiencies in excess of 50% are still more preferred.

B. Good Film Forming Ability
Emissive organic materials that form high quality pin-hole free films by evaporation, are preferred.

C. Good Thermal Stability
To ensure good thermal stability, the material should be designed to have a high glass transition temperature (Tg).

D. Balanced Carrier Injection and Transport
High efficiency light emitting diodes ("LEDs") require balanced carrier injection and transport. Ideally, the injection of holes at the anode and electrons at the cathode should be equal and the transport mobility of electrons and holes in the overall device should be equal.

Several classes of luminescent polymers have been disclosed in the art heretofore. These include, for example, poly[1,4-phenylene vinylene], PPV [J. H. Burroughs, D. D. C. Bradley, A. R. Brown, R. N. Marks, K. Mackay, R. H. Friend, P. L. Burns and A. B. Holmes, Nature 347, 539 (1990)], soluble derivatives of PPV, such as MEH-PPV [U.S. Pat. No. 5,189,136], Aryl-substituted-PPV [H. Spreitzer, W. Kreuder, H. Becher, H. Schoo, R. Demandt, German Pat. WO 98/27136], and PPV copolymers [European Patent 0544795, WO 9804610A1, H. Becker, H. Spreitzer, Y. Cao, Adv. Mater. 12(1), 42 (2000)]. Soluble derivatives of polythiophene are also known in the art, for example the poly(3-alkylthiophenes) [D. Braun, G. Gustafssom, D. Mcbranch, J. Appl. Phys. 72, 564 (1992)]. The photoluminescent spectra of these polymers typically fall in the visible spectral region with colors ranging from green to red. Considerable progress have been made toward using these materials in light emitting displays with lifetimes sufficient for commercial products [Chi Zhang, Gang Yu and Yong Cao, U.S. Pat. No. 5,798,170, Ian Park, Yong Cao and C. Y. Yang, J. Appl. Phys. 85(4), 2441 (1999)].

Low molar mass organic molecules can also be used for electroluminescence ("EL") applications [S. A. VanSlyke; C. H. Chen; C. W. Tang, Appl. Phys. Lett. 1996, 69 2160]. Disadvantages of these materials include their propensity for crystallization and difficulties in obtaining films by solution processing.

In response to the drawbacks of polymeric and low molar mass organic molecules for EL applications, there is intense interest in developing materials of intermediate dimensions with topological attributes that discourage crystallization. Examples include spiro-[Donald Lupo, Josef Salbeck, Hermann Schenk, Thomas Stehlin, Roland Stem, Arno Wolf U.S. Pat. No. 5,480,217] and trigonal star-shaped [Y. Shirota, J. Mater. Chem. 10, 1 (2000)] molecules. The choice of shape comes from consideration of how this molecular characteristic translates into a tendency of the bulk material to achieve an ordered lattice. Few guidelines are available for this purpose and new general structures that combine a preference to form useful films with the electrooptical requirements for EL are needed for the fabrication of more efficient LEDs. Examples of the use of a binaphthol framework as a suitable core for the synthesis of amorphous organic chromophores for EL applications has been reported [J. C. Ostrowski, R. A Hudack, M. R. Robinson, S. Wang, G. C. Bazan, Chem. Eur. J, 2001, 7(20), 4500].

SUMMARY OF THE INVENTION

One object of the present invention is to provide blue electroluminescent materials based on a binaphtyl compound of the general formula (I)

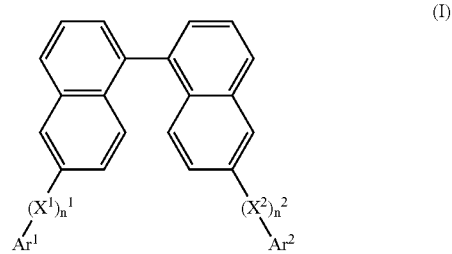

(I)

wherein each of $Ar^1$ and $Ar^2$ is independently a substituted or non-substituted aromatic hydrocarbon or a substituted or non-substituted aromatic heterocycle, each $X^1$ and $X^2$ is independently a substituted or non-substituted aromatic hydrocarbon, each $n^1$ and $n^2$ is independently 0 or 1, and wherein the compound's binaphtyl framework can optionally and independently have one or more substituent groups at any position except those occupied by $(X^1)n^1Ar^1$ and $(X^2)n^2Ar^2$.

The present invention also provides an organic light emitting device comprising a layer between an anode and a cathode, the layer including a binaphtyl compound of the present invention. The binaphtyl-containing layer can be an emissive layer, or can be in addition to an emissive layer, either as an additional emissive layer or as a hole-blocking layer. Preferably, the concentration of the binaphtyl compound in the layer is between about 0.01 to 20% by weight. If the binaphtyl-containing layer is an additional emissive layer, to the emissive layer, it can be placed either between the anode and emissive layer or between the emissive layer and cathode. If the binaphtyl-containing layer is, it can be placed either between the emissive layer and cathode.

The binaphthol compounds of the present invention can also be useful for fluorescent dyes, sensors and probes in various media including biological membranes and cells.

DETAILED DESCRIPTION OF THE INVENTION

Figure 1A:
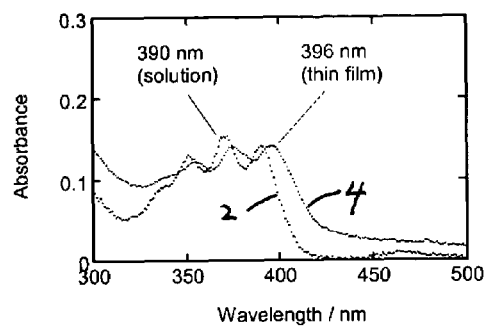
FIG. 1A is a graph showing the absorption of a binaphtyl compound in chloroform.

In the compound of formula (I), the $(X^1)n^1 Ar^1$ and $(X^2)n^2 Ar^2$ groups are preferably such as to provide for blue emitted light. Each $Ar^1$ and $Ar^2$ can be independently a substituted or non-substituted aromatic hydrocarbon or aromatic heterocycle. Examples of such aromatic hydrocarbon groups include the following.

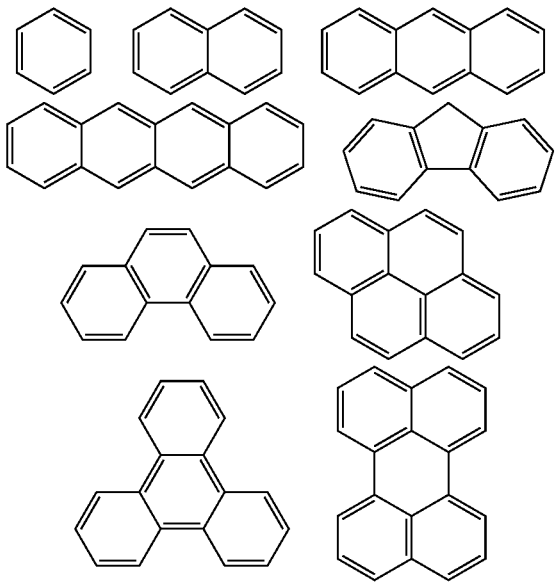

Examples of such aromatic heterocyclic groups include the following.

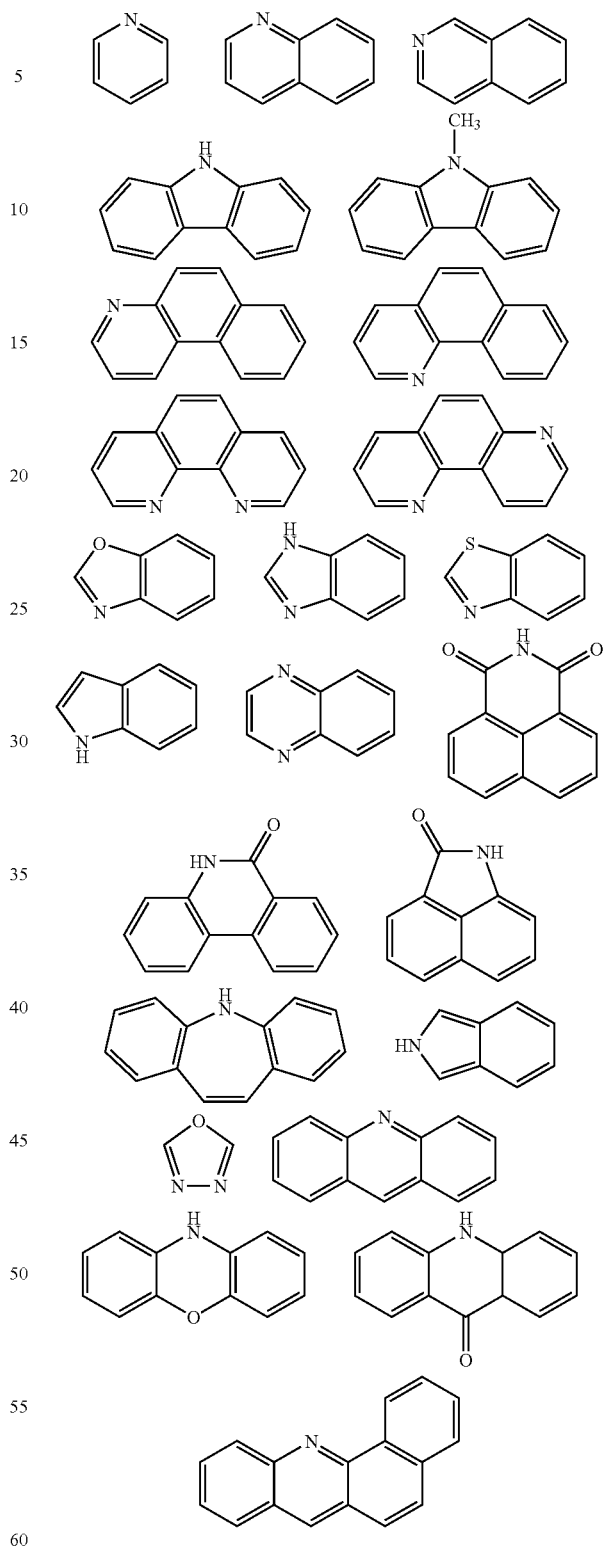

Preferably, both $Ar^1$ and $Ar^2$ are three, four or five-condensed aromatic rings. More preferably, both $Ar^1$ and $Ar^2$ are the same three, four or five-condensed aromatic rings. Examples of substituent groups on $Ar^1$ and $Ar^2$ include an alkyl group such as methyl group and ethyl group, an alkenyl group such as vinyl group, an alkoxy group such as methoxy group and ethoxy group, an alkoxycarbonyl group such as methoxycarbonyl group and ethoxycarbonyl group, and an aromatic group such as phenyl group.

In the compound, each $X^1$ and $X^2$ can be independently a substituted or non-substituted aromatic hydrocarbon. Preferably, both $X^1$ and $X^2$ are one, two or three-condensed aromatic rings such as the following.

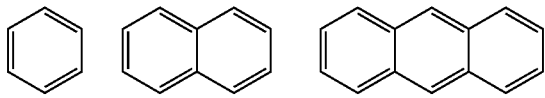

More preferably, both $X^1$ and $X^2$ are phenylene groups.
Preferably, the binaphtyl compound has the formula (II):

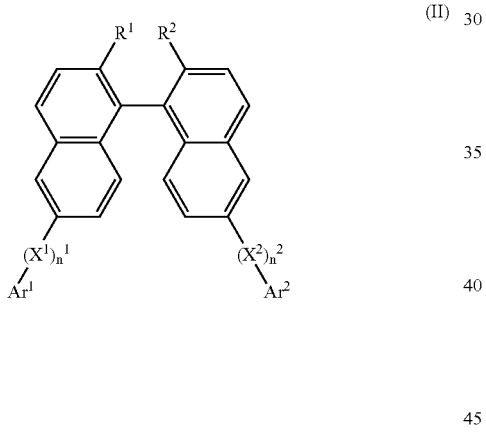

(II)

wherein the $(X^1)n^1Ar^1$ and $(X^2)n^2Ar^2$ groups are as described above and each $R^1$ and $R^2$ is independently a substituted or non-substituted alkyl group or alkoxy group. Examples of such alky groups include methyl, ethyl, propyl, butyl, sec-butyl, tert-butyl, pentyl, hexyl, heptyl, octyl, stearyl, 2-phenylisopropyl, trichloromethyl, trifluoromethyl, benzyl, α-phenoxybenzyl, α,α-dimethylbenzyl, α,α-methylphenylbenzyl, α,α-ditrifluoromethylbenzyl, triphenylmethyl and α-benzyloxybenzyl. Examples of such alkoxy groups include methoxy, ethoxy, propoxy, n-butoxy, t-butoxy, n-octyloxy, t-octyloxy, 1,1,1-tetrafluoroethoxy, phenoxy, benzyloxy and octylphenoxy.

Compounds of formula (II) have good solubilities in common organic solvents, resist crystallization and can be sublimed in a device fabrication process. These properties enable the fabrication of organic electroluminescent devices. The $R^1$ and $R^2$ groups are preferably chosen to control the glass transition temperature of the material. More preferably, for ease of synthesis, both $R^1$ and $R^2$ are alkoxy groups. Most preferably, both $R^1$ and $R^2$ are the same alkoxy groups. Also, in various embodiments, $R^1$ and $R^2$ can bind to each other to form a substituted or non-substituted ring structure. The binaphtyl framework of the compound of formula (I) or formula (II) can be substituted or non-substituted. A framework substituent can include a halogen atom such as fluorine, chlorine, bromine and iodine, a hydroxyl group, and substituted or non-substituted alkyl, alkenyl, alkoxy or alkoxycarbonyl group at any position except those occupied by $(X^1)n^1Ar^1$, $(X^2)n^2Ar^2$. Examples of such substituted or non-substituted groups include an alkyl group such as methyl group and ethyl group, an alkenyl group such as vinyl group, an alkoxy group such as methoxy group and ethoxy group, and an alkoxycarbonyl group such as methoxycarbonyl group and ethoxycarbonyl group, all of which may have substitutents.

The binaphthol compounds of the present invention can be prepared by methods which are well known in the literature. Typical procedures are described in standard works on organic synthesis, e.g. Houben-Weyl, Methoden de Organischen Chemie (Methods of Organic Chemistry), Georg-Thieme-Verlag, Stuttgart and in the appropriate volumes of the series "The Chemistry of heterocyclic Compounds" by A. Weissberger and E. C. Taylor (editors). The preparations described herein are carried out under reaction conditions which are known and suitable for said reactions. Variations of these reaction conditions are well known in the literature.

Suitable binaphtyl derivatives according to the present invention are as follows:

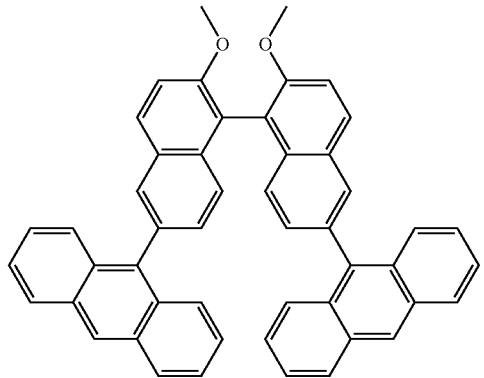

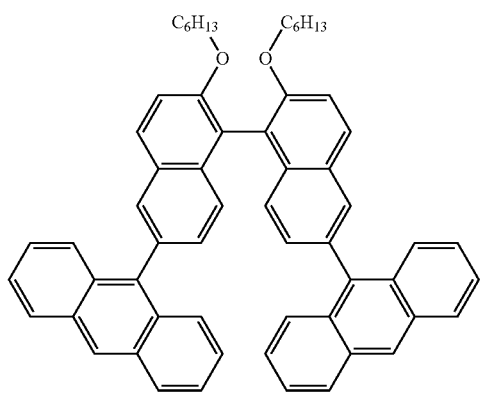

-continued
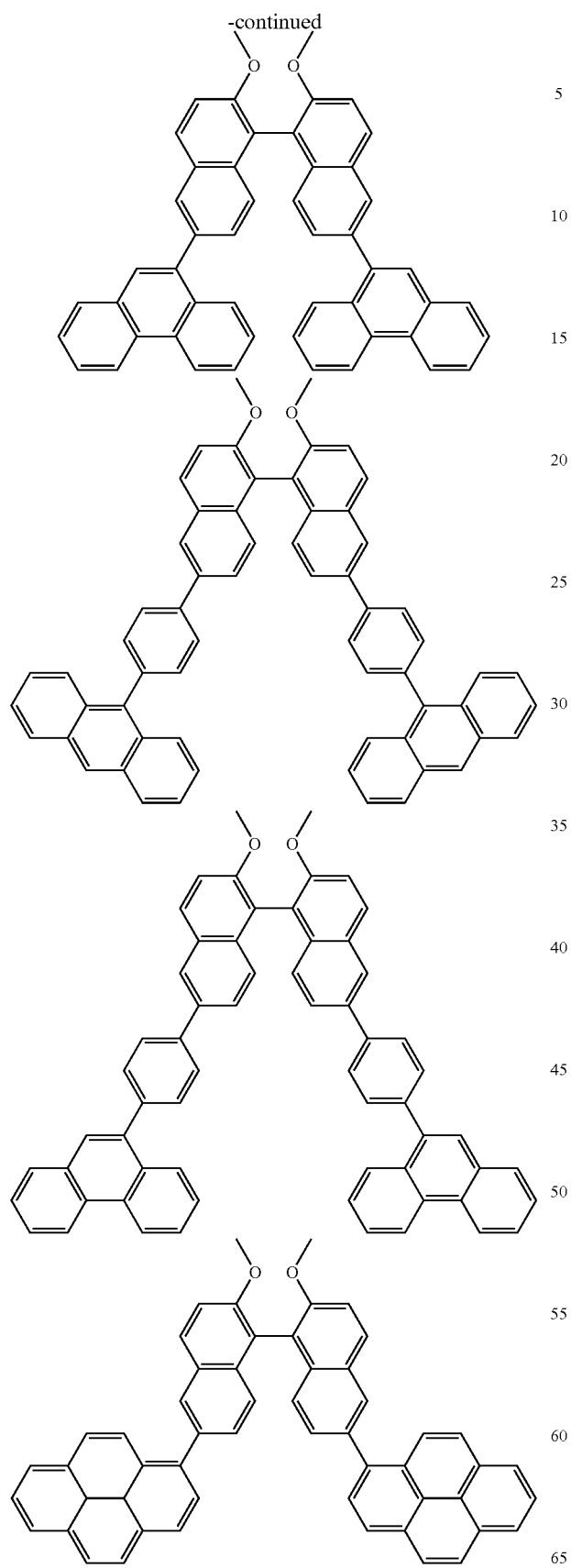
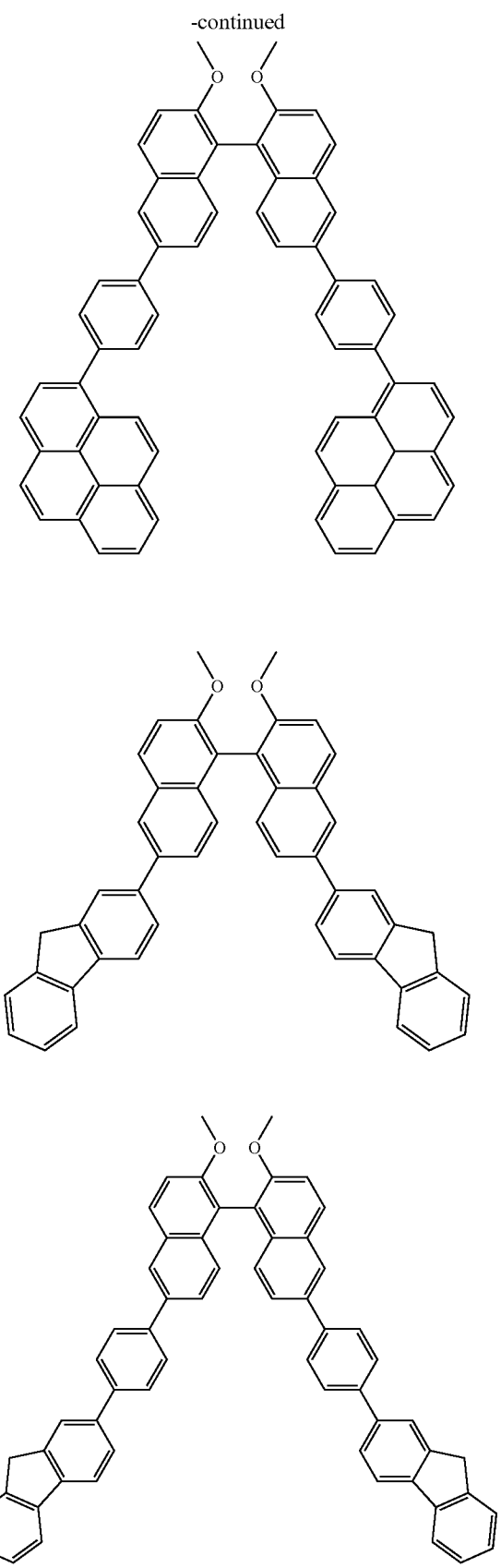

-continued
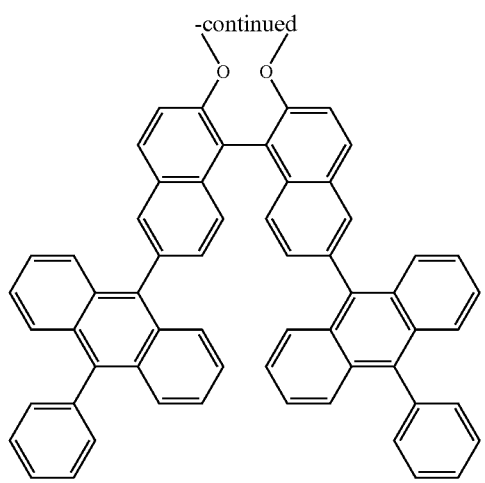
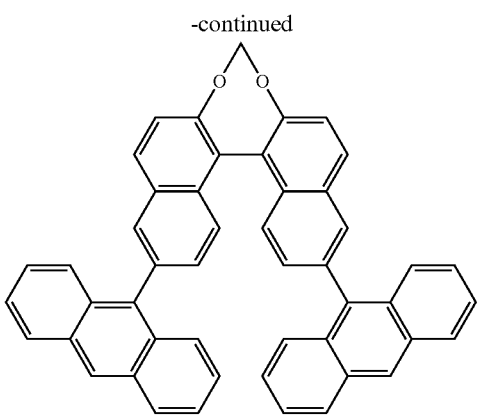

-continued
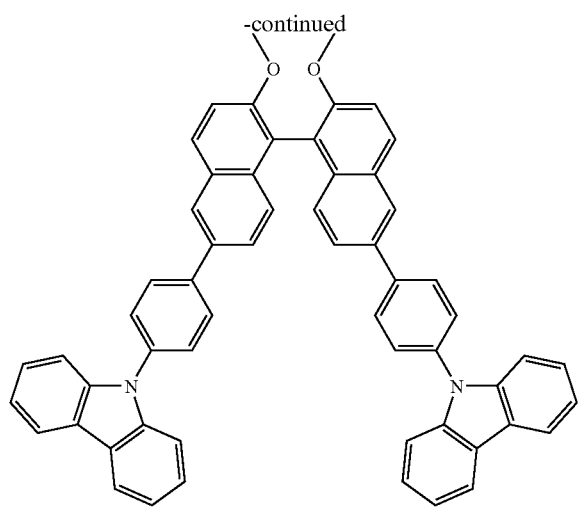
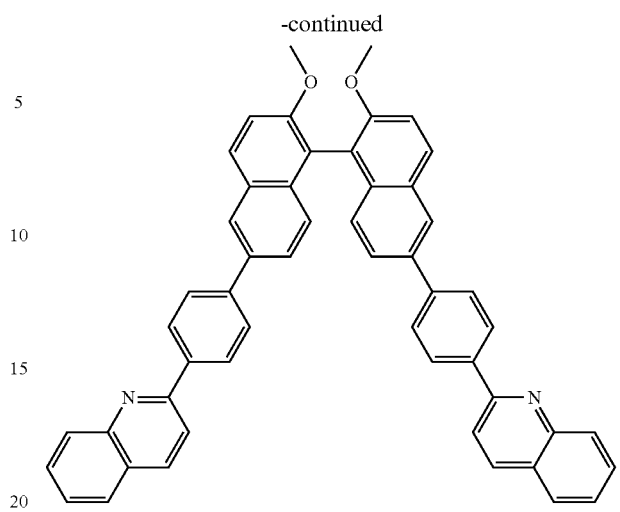
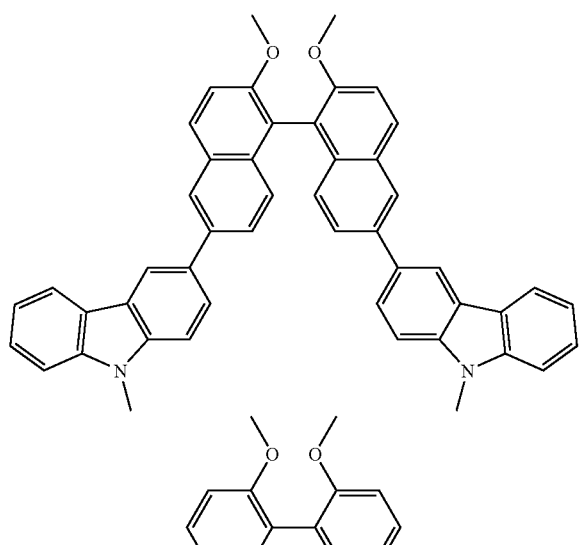
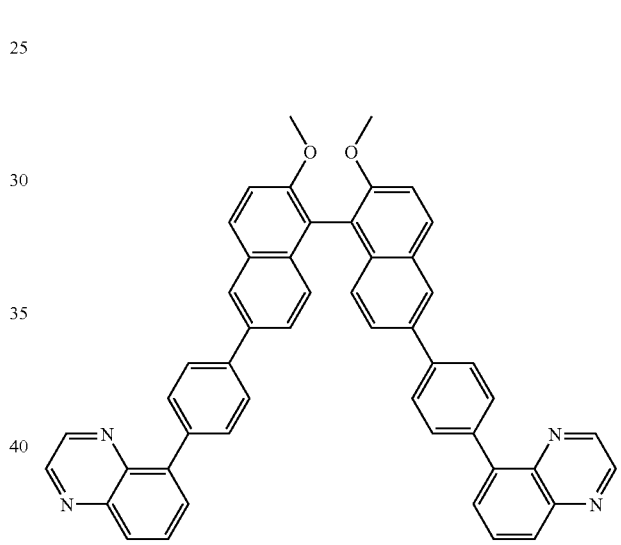
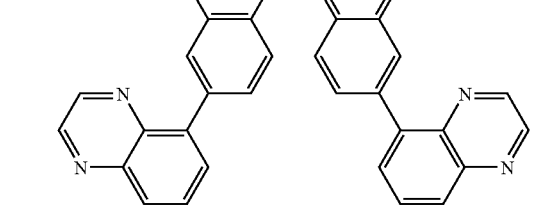
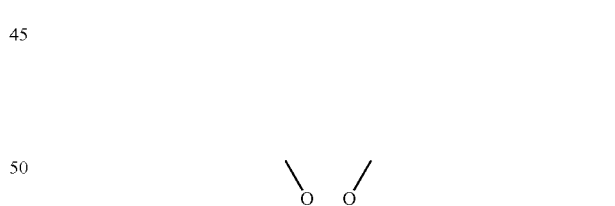
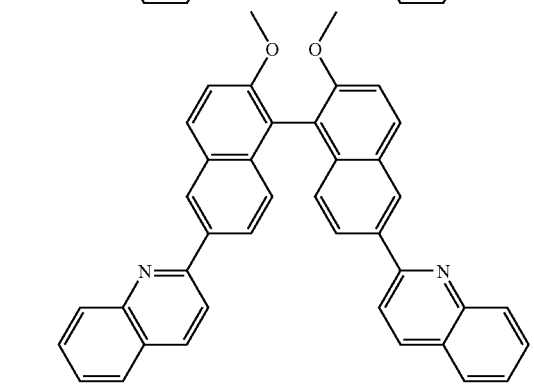
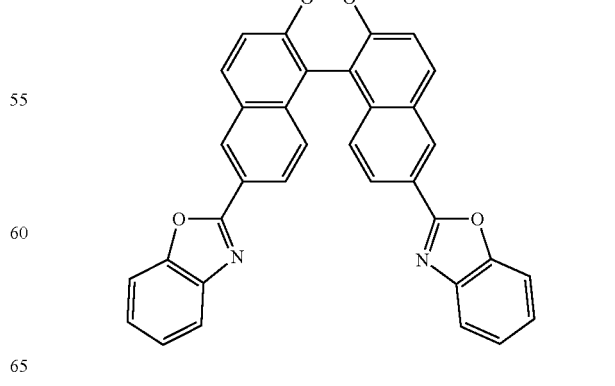

-continued
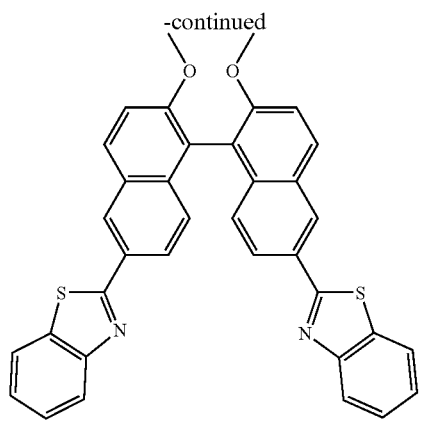
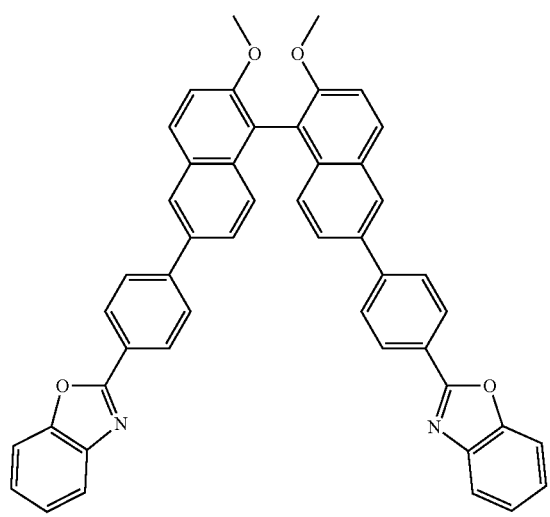
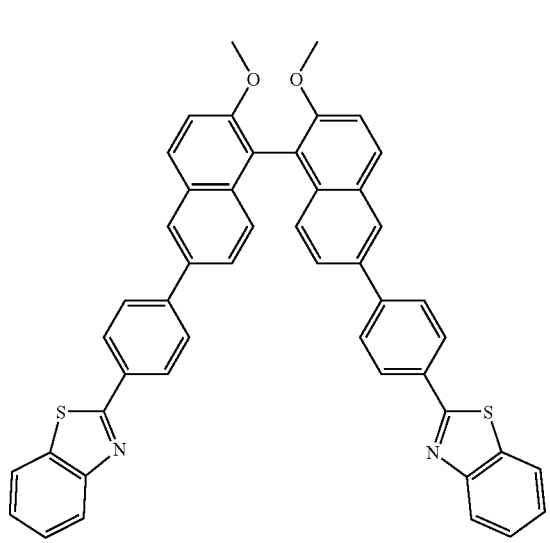
-continued
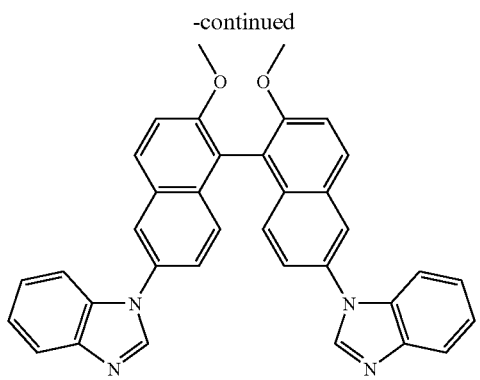
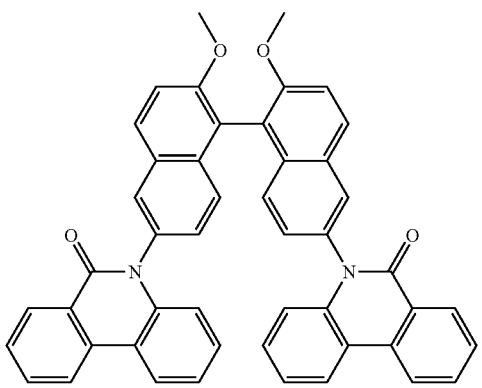
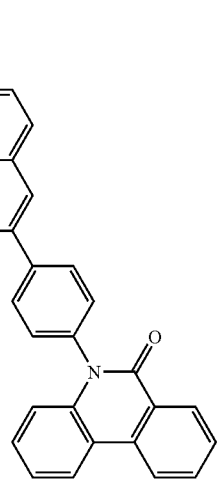

-continued
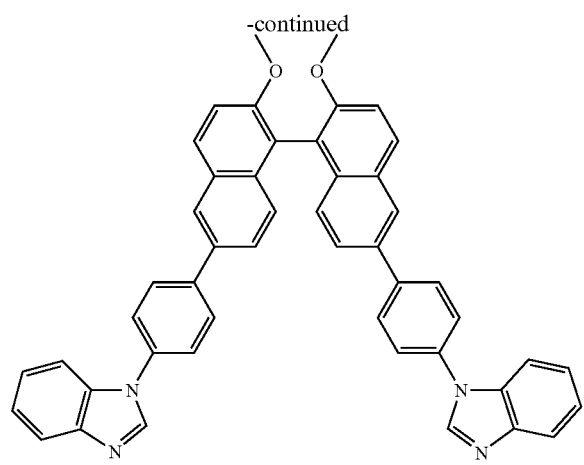
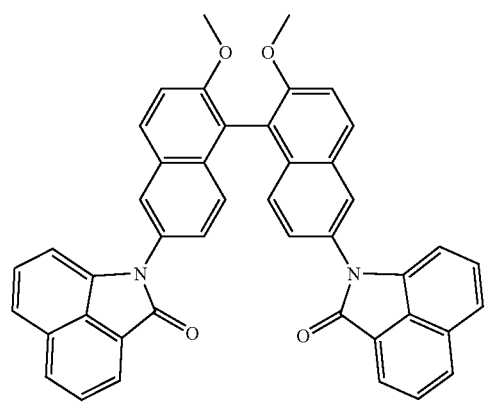
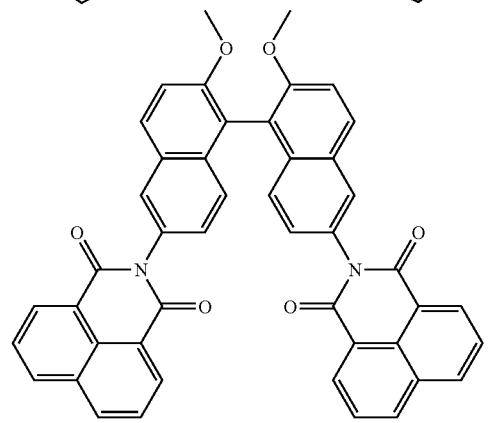
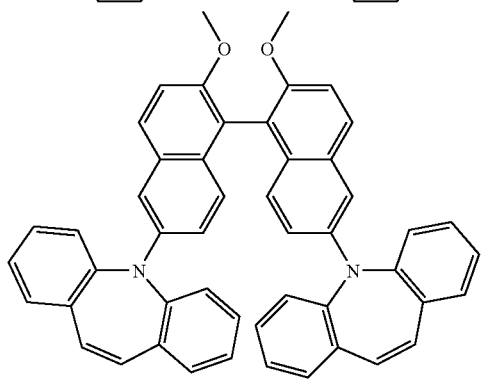
-continued
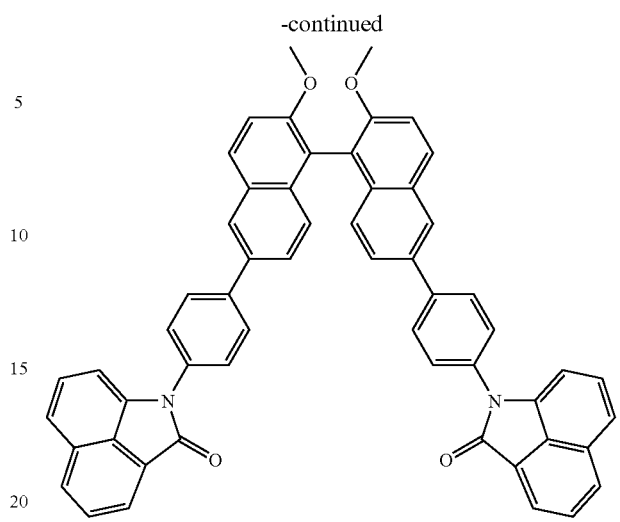
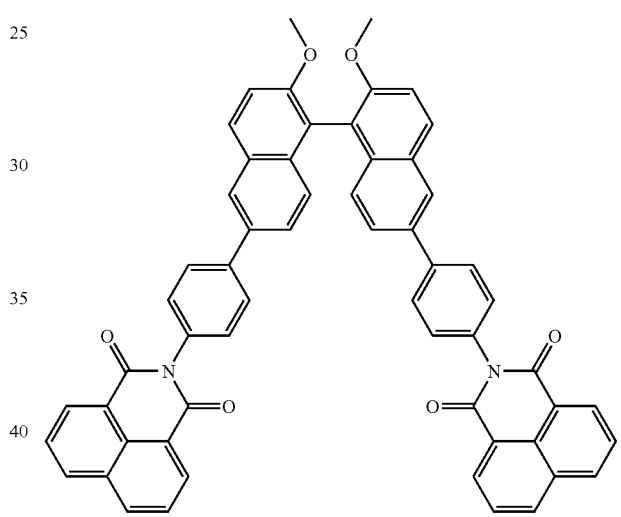
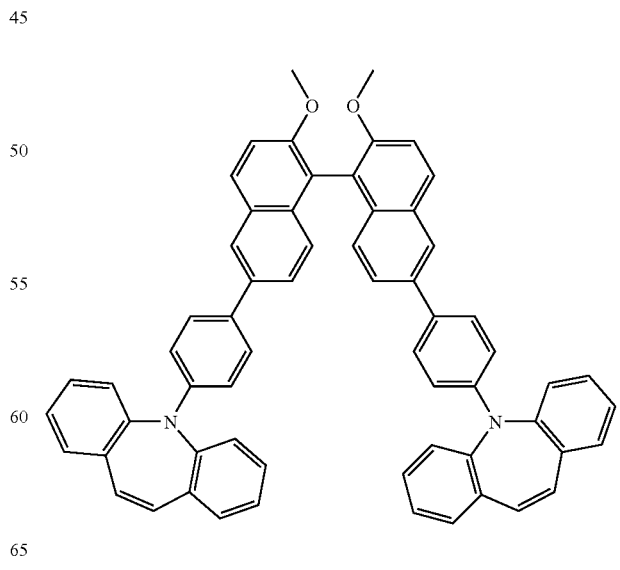

-continued
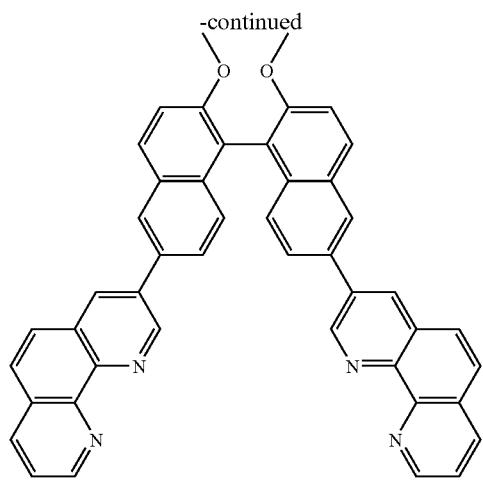
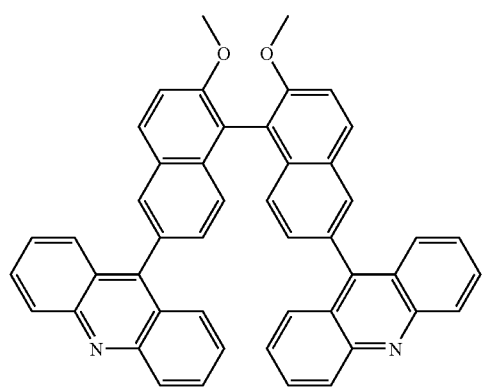
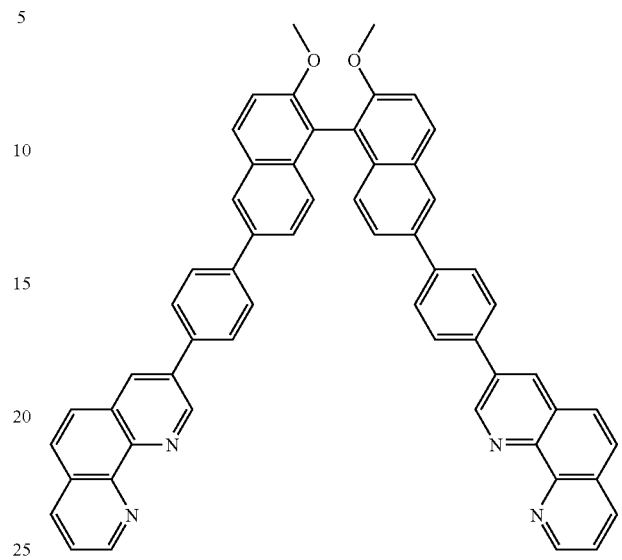
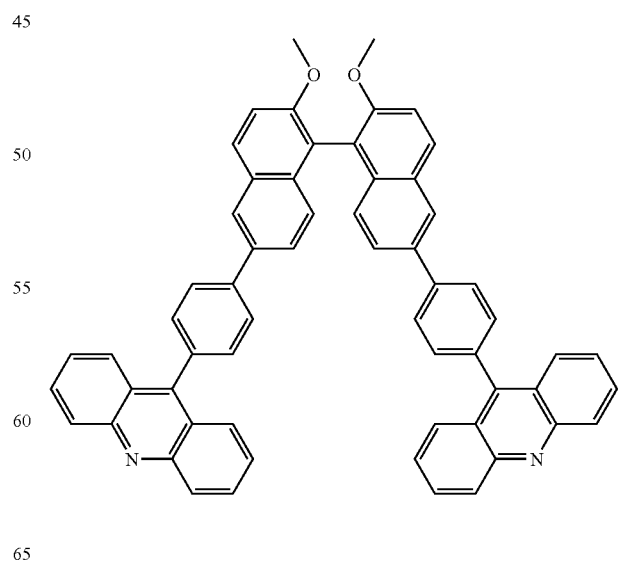
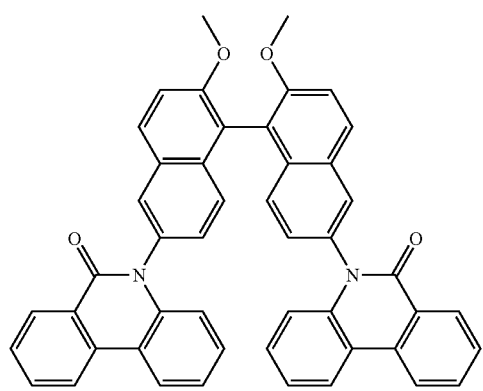

19
-continued
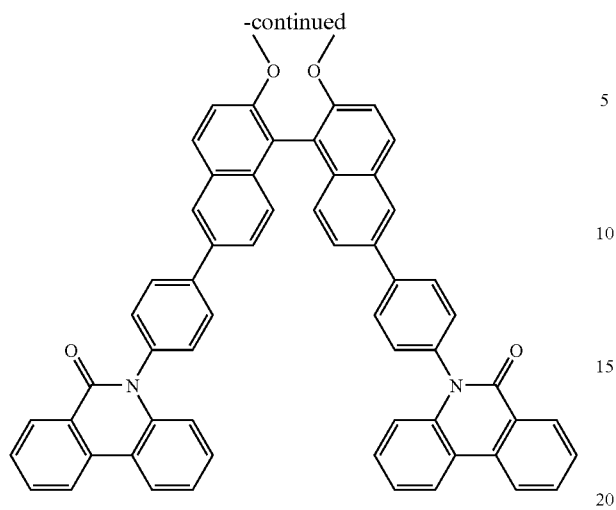
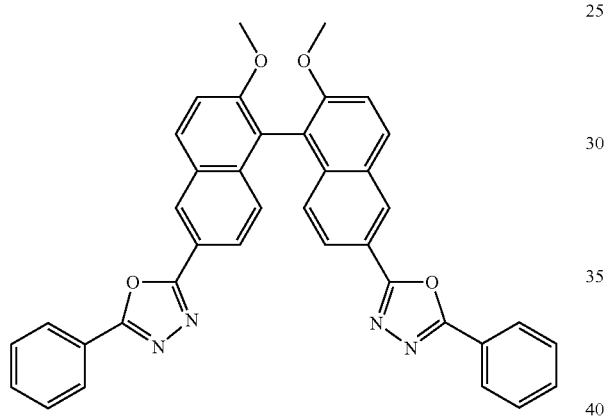
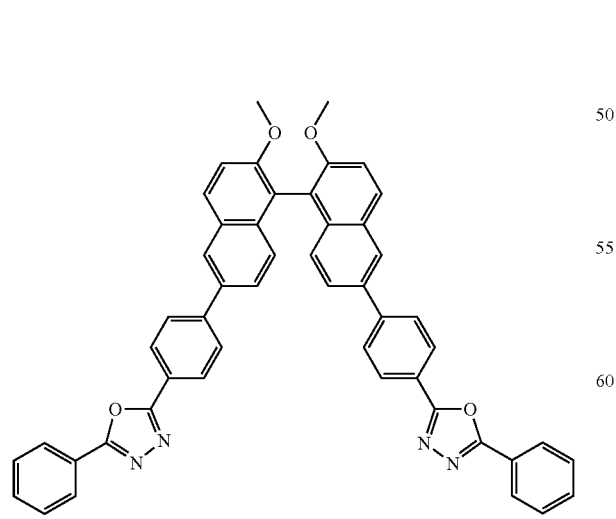
20
-continued
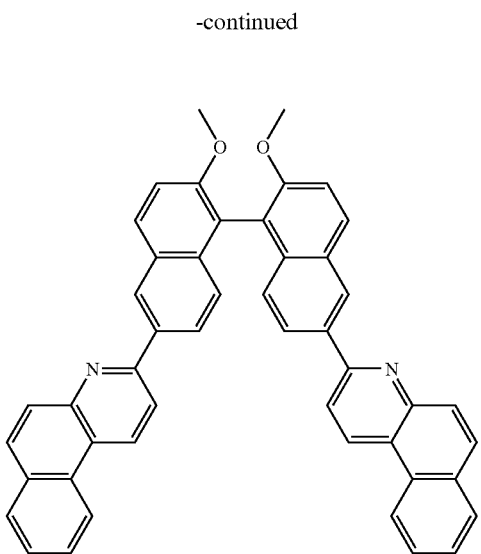
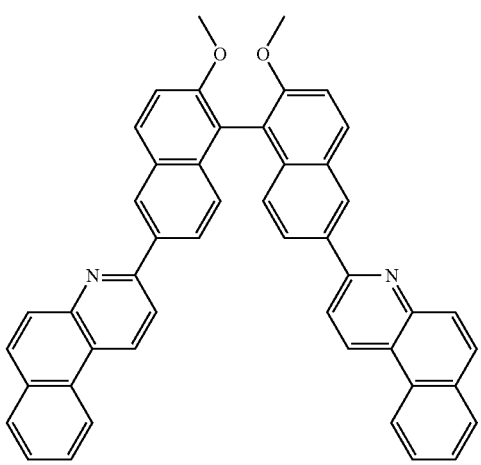

-continued
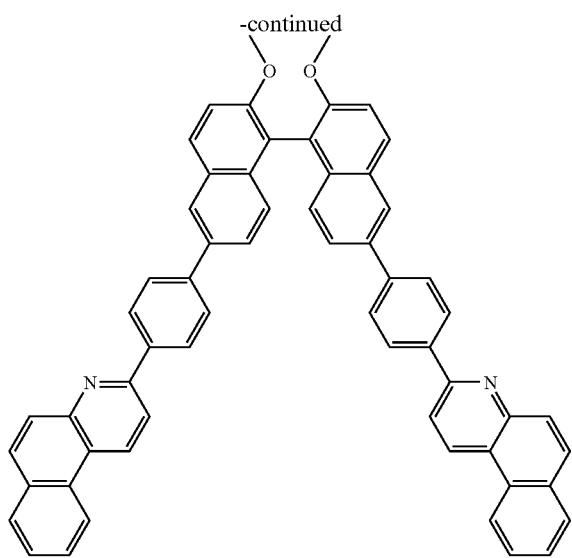
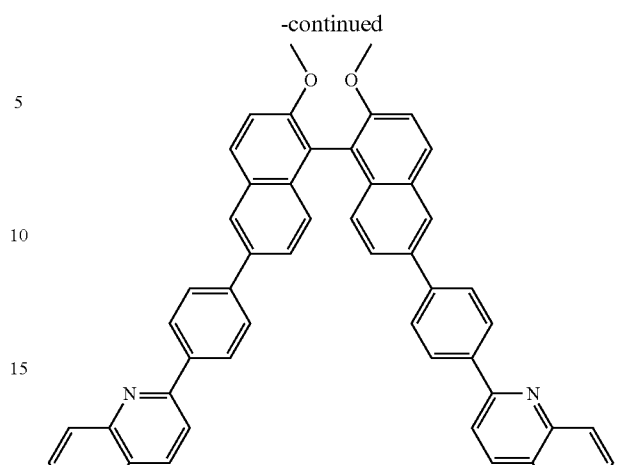
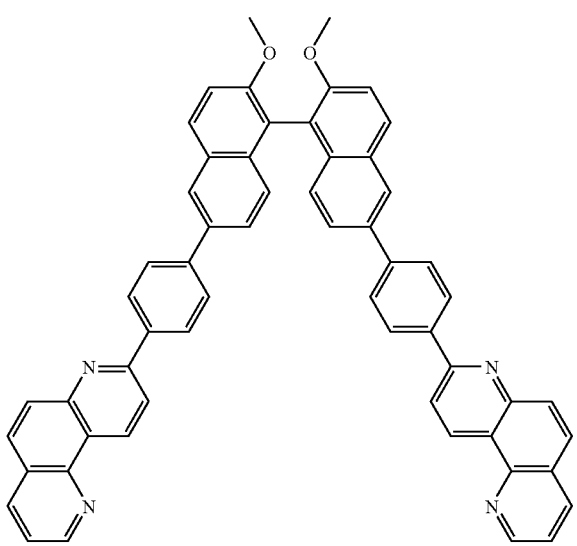
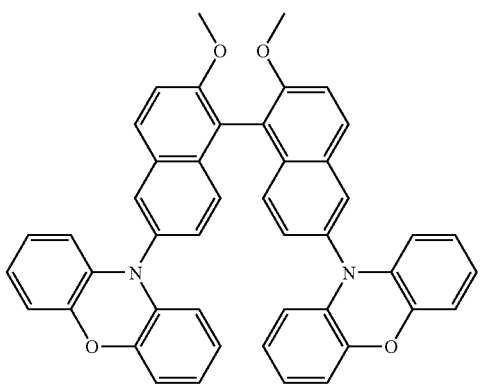
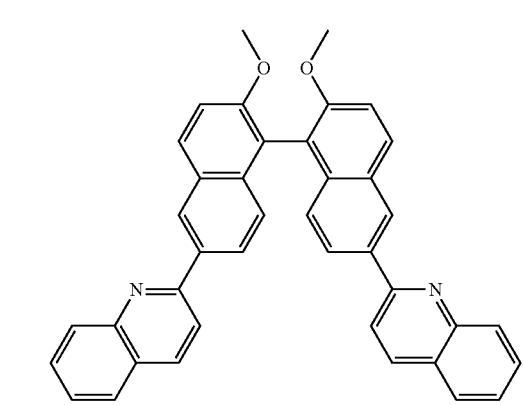
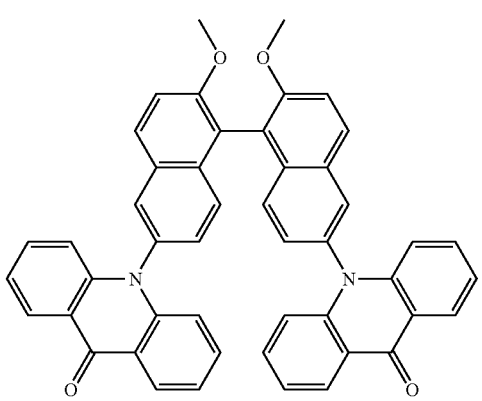

-continued

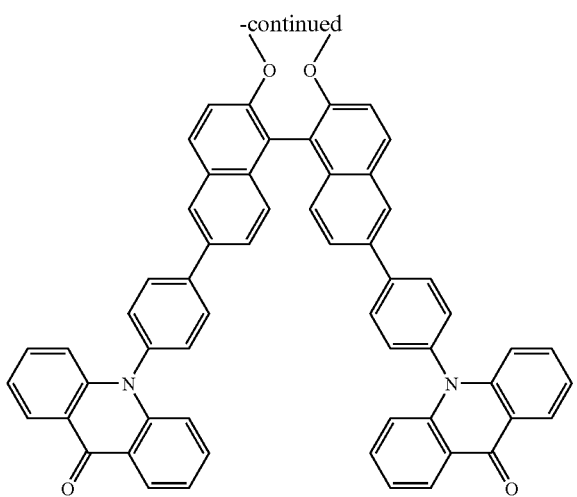

The binaphtyl compounds shown herein can have strong fluorescence intensity and thermal stability. Therefore, stable luminescent performance can be achieved by using the binaphtyl compounds in organic luminous layers of organic electroluminescent devices.

The construction of an organic electroluminescent device according to the present invention is described below by reference to FIG. 3. However, the present invention is not limited thereto.

Figure 3:
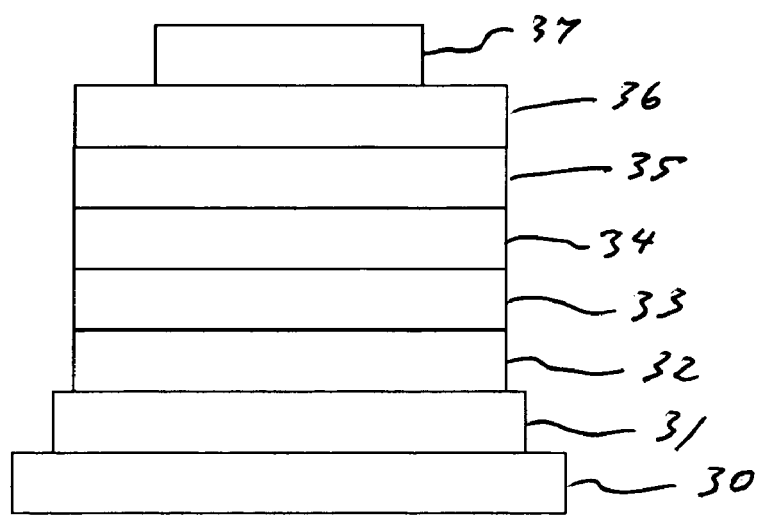
FIG. 3 is a sketch of an electroluminescent device.

An embodiment of an organic electroluminescent device according to the present invention is shown in FIG. 3 of Example 4, below, in a schematic sectional view. Referring to FIG. 3, the construction of an organic electroluminescent device of the present invention can be described as follows.

An anode 31 is deposited on a substrate 30 The substrate becomes a support of the organic electroluminescent device and can be, for example, a plate of quartz or glass, a metal sheet or foil, or a plastic film or sheet. In particular, a glass plate or a transparent synthetic resin plate such as polyester or polymethacrylate is preferred. In the case of using a synthetic resin substrate, it is necessary to take notice of the gas-barrier property. If the substrate has excessively low gas-barrier property, the organic electroluminescent device may disadvantageously deteriorate due to outside air passing through the substrate. Accordingly, a dense silicon oxide film or the like is provided at least on one surface of the synthetic resin substrate to ensure the gas-barrier property, and this is one of the preferred methods.

The anode 31 fills the role of injecting holes into a hole-transporting layer 33. The anode is generally composed of a metal such as aluminum, gold, and silver, a metal oxide such as indium oxide and/or tin oxide, a metal halide such as copper iodide, a carbon black or an electrically conductive polymer such as poly(3-methyl thiophene), polypyrrole or polyaniline. The anode is usually formed by sputtering or vacuum vapor deposition. In the case where a metal fine particle of silver, a fine particle of copper iodide, carbon black, an electrically conductive metal oxide fine particle or an electrically conductive polymer fine particle is used, the anode can be formed by dispersing this in an appropriate binder resin solution and applying the dispersion solution on the substrate. Furthermore, in the case of using an electrically conductive polymer, the anode can be provided by forming a thin film directly on the substrate using electrolytic polymerization or by coating the electrically conductive polymer on the substrate (see, Appl. Phys. Lett., Vol. 60, page 2711 (1992)).

The anode 31 may also be a stacked layer structure formed by stacking layers comprising different materials.

The thickness of the anode 31 varies depending on the required transparency. In the case where the transparency is necessary, the transmittance of visible ray is usually set to about 60% or more, preferably about 80% or more, and in this case, the thickness is usually from about 5-1,000 nm, preferably on the order of about 10-500 nm. In the case where the transparency is not required, the anode 31 may have substantially the same thickness as the substrate 30. A different electrically conductive material can also be further stacked on the anode.

On the anode 31, a hole-transporting layer 33 is provided. The material for the hole-transporting layer preferably ensures high efficiency in the hole injection from the anode and efficient transportation of the injected holes. To satisfy these requirements, the material preferably has a small ionization potential, a high transparency to visible ray, a high hole mobility, excellent stability and difficulty of generating impurities serving as a trap during the production or use. Since the hole-transporting layer 33 contacts a light-emitting layer 34, the material for the hole-transporting layer preferably does not quench the light emission from the light-emitting layer 34 and preferably does not form an exciplex between the hole-transporting layer 33 and the light-emitting layer 34 which otherwise would reduce the efficiency. In addition to these general requirements, when the device is required to have heat resistance, such as when the device is mounted on vehicles, the material preferably has a Tg of about 75° C. or more, and preferably, about 85° C. or more.

Examples of the hole-transporting material include aromatic diamines containing two or more tertiary amines and having two or more condensed aromatic rings substituted to nitrogen atoms, represented by 4,4'-bis[N-(1-naphthyl)-N-phenylamino]biphenyl (see, JP-A-5-234681); aromatic amine compounds having a star burst structure, such as 4,4', 4"-tris(1-naphthylphenylamino)triphenylamine (see, J. Lumin., Vol. 72-74, page 985 (1997)); aromatic amine compounds comprising a tetramer of triphenylamine (see, Chem. Commun., page 2175 (1996)); and spiro compounds such as 2,2',7,7'-tetrakis(diphenylamino)-9,9'-spirobifluorene (see, Synth. Metals, Vol. 91, page 209 (1997)). These compounds can be used individually or in combination.

In the case of forming the hole-transporting layer 33 by the coating method, one or more hole-transporting materials are dissolved to prepare a coating solution and the coating solution is coated on the anode 31 by spin coating or the like and dried to form the hole-transporting layer 33. If desired, the hole-transporting materials can be dissolved after adding additives which do not become a trap for the holes, such as binder resin and coatability improving agent. Examples of the binder resin include polycarbonate, polyarylate and polyester. If the amount of the binder resin added is large, the hole mobility is reduced. Therefore, the amount added thereof is preferably as low as possible and in terms of the content in the hole-transporting layer 33, preferably about 50% by weight or less.

In the case of forming the hole-transporting layer 33 by the vacuum vapor deposition method, the hole-transport material is placed in a crucible disposed within a vacuum container, the inside of the vacuum chamber is evacuated to about $10^{-4}$ Pa by an appropriate vacuum pump and then the crucible is heated to evaporate the hole-transport material, whereby the hole-transporting layer 33 is formed on the substrate having formed thereon the anode 31 and being disposed to face the crucible.

The thickness of the hole-transporting layer 33 is usually from about 5-300 nm, preferably from about 10-100 nm. In order to uniformly form such a thin film, the vacuum vapor deposition method is generally used in many cases.

To improve the contact between the anode 31 and the hole-transporting layer 33, a hole injection layer 32 may be formed between the anode and the hole-transporting layer. The material to be used for the hole injection layer preferably makes good contact with the anode, is able to form a uniform thin film, is thermally stable i.e. has a high melting point and a high glass transition temperature, the melting point being at a level of at least about 300° C., and the glass transition temperature being at least about 100° C. Further, it is preferable that the ionization potential is low, the hole injection from the anode is easy, and the hole mobility is large. For this purpose, an organic compound such as a porphyrin derivative or a phthalocyanine compound (JP-A-63-295695), a starburst type aromatic triamine (JP-A-4-308688), polythienylenevinylene or poly-p-phenylenevinylene (JP-A-4-145192), or polyaniline (Appl. Phys. Lett., vol. 64, p. 1245, 1994) has heretofore been reported.

A porphyrin compound or a phthalocyanine compound may be mentioned as a compound which is frequently used as a material for the above hole injection layer. Such a compound may or may not have a center metal.

The following compounds may be mentioned as specific examples of such preferred compounds: Porphine, 5,10,15, 20-tetraphenyl-21H,23H-porphine, 5,10,15,20-tetraphenyl-21H,23H-porphine cobalt(II), 5,10,15,20-tetraphenyl-21H, 23H-porphine copper(II), 5,10,15,20-tetraphenyl-21H,23H-porphine zinc(II), 29H,31H-phthalocyanine, Copper(II) phthalocyanine, and Zinc(I) phthalocyanine.

Also in the case of the hole injection layer 32, a thin film may be formed in the same manner as for the hole-transporting layer. However, in the case of an inorganic material, a sputtering method, an electron beam vapor deposition method or a plasma CVD method may further be employed.

The thickness of the hole injection layer 32, formed as described above, is usually from about 3-100 nm, preferably from about 10-50 nm.

On the hole-transporting layer 33, a light-emitting layer 34 is provided. Applied with an electric field between the electrodes, a hole injected from the anode 31 and transferring through the hole-transporting layer 33 and an electron injected from a cathode 37 and transferring through a hole-blocking layer 35 are recombined and thereby the light-emitting layer is excited and emits strong light.

A binaphtyl compound of the present invention may be included in the light-emitting layer 34.

A binaphtyl compound according the present invention can be used alone as a light-emitting material in the light-emitting layer 34. Usually, fluorescent dyes may not be applicable to such use because most fluorescent dyes have poor thin film forming ability. Also, the intermolecular interaction between the fluorescent dyes may cause a decrease in luminous efficiency by quenching effect. However, the binaphtyl compounds of the present invention possess good thin-film forming ability and less intermolecular interaction because of a bulky, rigid binaphtyl backbone. Such properties allow suitable binaphtyl compounds of the present invention to be used alone in the light-emitting layer 34 and still maintain their high luminous efficiency.

A binaphtyl compound of the present invention can also be used with other light emitting materials. Usually, the light-emitting layer 34 comprises (1) a host material having electron-transporting property or hole-transporting property and (2) a dopant dye capable of light emission at room temperature. Using a host material and a dopant dye has the following advantages: (1) the luminous efficiency is improved by the highly efficient fluorescent dye; (2) the luminescent wavelength can be changed by the selection of the fluorescent dye; (3) it is possible to use a fluorescent dye which undergoes quenching; and (4) a fluorescent dye having a poor thin film forming property can be used. Also for the purpose of improving the driving life of the device, it is effective to dope a fluorescent dye in the host material.

A binaphtyl compound of the present invention can be used as either the host material or the dopant dye.

In the case where the binaphtyl compound is used as the host material, substituent groups bound with the binaphtyl backbone may be chosen in order to possess appropriate hole or electron mobility. A preferred dopant dye is the green phosphorescent dye fac-tris(2-phenylpyridine) iridium(III) [Ir(ppy)3], which is particularly useful with binaphtyl compounds derived from carbazole. Other dopant dyes that can be used include, for example, a naphthacene derivative represented by rubrene (JP-A-4-335087), a quinacridone derivative (JP-A-5-70773), or a condensed polycyclic aromatic ring such as perylene (JP-A-5-198377).

In the case where the binaphtyl compound is used as the dopant dye, the host material can be a metal complex such as an aluminum complex of 8-hydroxyquinoline (JP-A-59-194393), an oxadiazole derivative (JP-A-2-216791), a bisstylylbenzene derivative (JP-A-1-245087, JP-A-2-222484), a rare earth complex (JP-A-1-256584), or a carbazole derivative (JP-A-2000-21572).

The content of the dopant dye is preferably from about 0.1-30% by weight based on the entire light-emitting layer 34. If the content is less than about 0.1% by weight, the dopant dye may fail to sufficiently contribute to the improvement of light emission efficiency of the device, whereas if the dye exceeds about 30% by weight, concentration quenching may occur to cause reduction of the light emission efficiency.

The host material and the dopant dye may be uniformly distributed within the light-emitting layer or may be non-uniformly present by having a distribution in the film thickness direction.

The thickness of the light-emitting layer 34 is usually from about 10-200 nm, preferably from about 20-100 nm. The thin film can be formed by the same method as the hole-transporting layer 33.

A hole-blocking layer 35 is stacked on the light-emitting layer 34 to come into contact with the interface of the light-emitting layer 34 in the cathode side and fills the role of inhibiting the holes transferring from the hole-transporting layer 33, from reaching a cathode 37. The hole-blocking layer 35 is preferably formed of a compound capable of transporting the electrons injected from the cathode 37 toward the direction of the light-emitting layer 34 with good efficiency. The material, constituting the hole-blocking layer preferably has a high electron mobility and low hole mobility. The hole-blocking layer has a function of enclosing holes and electrons within the light-emitting layer 34 and thereby improving the light emission efficiency.

Examples of the hole-blocking material satisfying these requirements include mixed ligand 8-quinolinolato complexes or other compounds will known in the art (for example, see: JP-A-11-273867). In accordance with a specific embodiment of the invention, a binaphtyl compound of the present invention can be used a the hole-blocking material, e.g., the binaphtyl compound of formula(I), preferably of formula (II).

A binaphtyl compound that is particularly useful as a hole-blocking material has the formula:

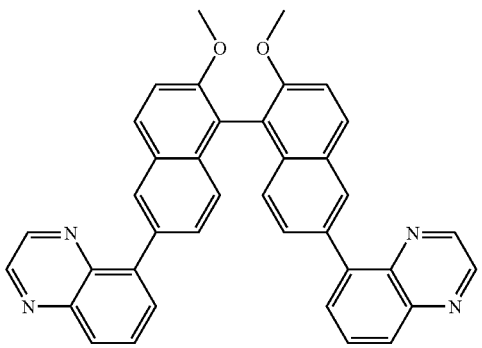

The cathode 37 performs a role of injecting electrons into the organic luminescent layer. The material to be used for the cathode may be a material to be used for the anode. However, to carry out the electron injection efficiently, the cathode is preferably a metal having a low work function, particularly a metal with about 4.7 eV or less. Such a material may, for example, be a metal such as tin, magnesium, indium, calcium, aluminum or silver, or an alloy containing such a metal as the main component. Among them, silver, magnesium, aluminum, indium or an alloy containing such a metal as the main component, is preferred. Otherwise, it is possible to employ a cathode having a trace amount of a metal having a low work function doped on a relatively stable metal. Such a cathode may, for example, be a metal film having from about 0.01-0.1% of lithium doped on aluminum or indium (JP-A-5-159882, JP-A-5-198380).

The thickness of the cathode 37 is usually from about 0.1 nm-10 microns, preferably from 0.2 nm to 2 microns.

To improve the electron injection efficiency from the cathode 37 to the hole-blocking layer 35, an electron-transporting layer 36 may be formed between cathode and hole-blocking layer. The electron-transporting layer is preferably formed by a compound which is capable of efficiently transporting electrons from a cathode in the direction of the hole-transporting layer 33 between electrodes to which an electric field is applied.

The electron-transporting compound to be used for the electron-transporting layer 36 is preferably a compound which has a high efficiency for electron injection from the cathode and which is capable of efficiently transporting the injected electrons. For this purpose, the compound preferably has a large electron affinity and whereby the electron mobility is large and excellent in stability, and impurities which are likely to constitute traps, are scarcely formed during the production or during use.

Material satisfying such conditions include an aromatic compound such as tetraphenylbutadiene (JP-A-57-51781), a metal complex such as an aluminum complex of 8-hydroxyquinoline (JP-A-59-194393), a metal complex of 10-hydroxybenzo[h]quinoline (JP-A-6-322362), a mixed ligand aluminum chelate complex (JP-A-5-198377, JP-A-5-198378, JP-A-5-214332, JP-A-6-172751), an oxadiazole derivative (JP-A-2-216791), a bisstylylbenzene derivative (JP-A-1-245087, JP-A-2-222484), and a p-phenylene compound (JP-A-3-33183).

The thickness of the electron-transporting layer 36 is usually from about 10-200 nm, preferably from about 30-100 nm. The electron-transporting layer may be formed by the same method as the hole-transporting layer 33, but a vacuum vapor deposition method is usually employed.

Moreover, to achieve good device performance, an ultra-thin layer of LiF, $MgF_2$, or $Li_2O$ (thickness of about 0.1-5 nm) can be formed between cathode 37 and electron-transporting layer 36, or between cathode 37 and light-emitting layer 34 (Appl. Phys. Lett., 70, 152, 1997; IEEETrans. Electron. Devices, 44, 1245, 1997).

While the binaphtyl compounds of the present invention can be preferably used in the light-emitting layer 34, they may also be used in the hole-transporting layer 33, hole-blocking layer 35, or electron-transporting layer 36, by choosing appropriate substituent groups which are bound to the binaphtyl backbone.

Although the construction of an organic electroluminescent device is described herein, the present invention is not limited thereto.

The present invention may be better understood by referring to the following examples.

EXAMPLE 1

This example describes the synthesis and characterization of a binaphtyl compound of the formula (III).

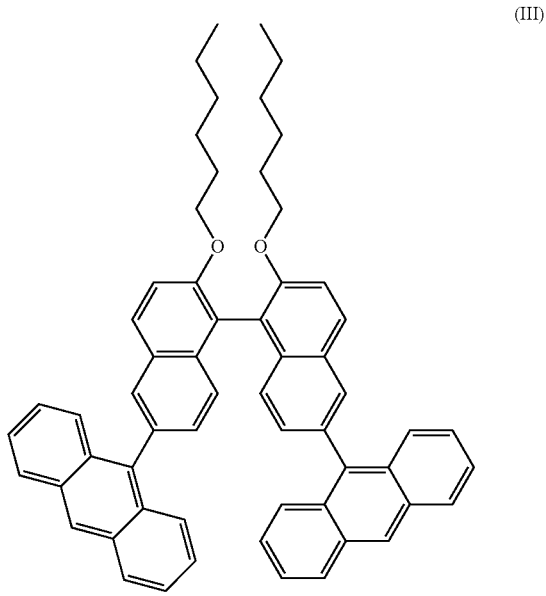

9-Anthracene boronic acid (130 mg, 0.585 mmol, 2.4 equivs) was dissolved in 20 mL ethanol and poured into a mixture of 6,6'dibromo-2,2'dihexyloxy-1,1'-binaphthyl (0.15 g, 0.244 mmol, 1 equiv) in toluene/water (40/20 ml). Sodium bicarbonate (1.06 g, 10 mmol in 20 ml water), Palladium tetrakis(triphenylphosphine) $Pd(PPh_3)_4$ (28.2 mg, 0.0244 mmol, 0.10 equivs) were then added to the mixture. The solution was degassed three times and the mixture was heated under Argon at 109° C. for 48 hrs. The solution was cooled down, the solvent evaporated, water was added and the aqueous phase was extracted with chloroform three times. The combined organic phases were washed with brine, dried, and the solution was concentrated under vacuum to afford the crude product. The resulting solid was purified by flash column chromatography on silica gel. (Hexanes 65%, chloroform 35%) to afford the compound of formula (III) (107 mg, 53%). The compound of formula (III) was subsequently purified by sublimation (sublimation temperature: 290° C., 0.07 Pa). Exact mass FAB (M+) calcd for $C_{60}H_{54}O_2$ 806.41, found: 806.41. 1H NMR (400 MHz $CDCl_3$): δ 8.53 (s, 2H), 8.04 (m, 10H), 7.78 (m, 4H), 7.45 (m, 12H), 4.13 (m, 4H), 1.55 (m, 4H), 1.14 (m, 12H), 0.82 (t, J=7.2 Hz, 6H), 13C NMR (100 MHz, $CDCl_3$): δ 148.1, 137.8, 134.1, 131.9, 131.0, 130.6, 130.3, 130.0, 129.8, 128.9, 127.7, 127.0, 126.2, 125.8, 125.7, 125.6, 121.4, 116.9, 70.53, 32.0, 29.9, 25.9, 23.0, 14.6.

DSC measurements on the compound of formula (III) (4 mg; Temp; 10 deg/min) showed a glass transition at 81.9° C.

Cyclic voltametric measurements for the compound of formula (III) (1 mM compound in 0.1 M tetrabutylammonium perchlorate (TBAP) in $CH_2Cl_2$; WE: glassy carbon, CE: Pt, RE: Ag): The redox potentials of the compound of formula (III) were determined with respect to the ferrocene/ferrocenium redox couple ($E_{1/2}$(Fc/Fc+)=0.41 V vs. SCE from a methylene dichloride solution (1 mM), the scan rate was 100 mv/s. These measurements showed irreversible oxidation at +1.20 V (vs. SCE) and reduction at −2.15 V (vs. SCE).

EXAMPLE 2

This example describes the synthesis and characterization of a binaphtyl compound of the formula (IV).

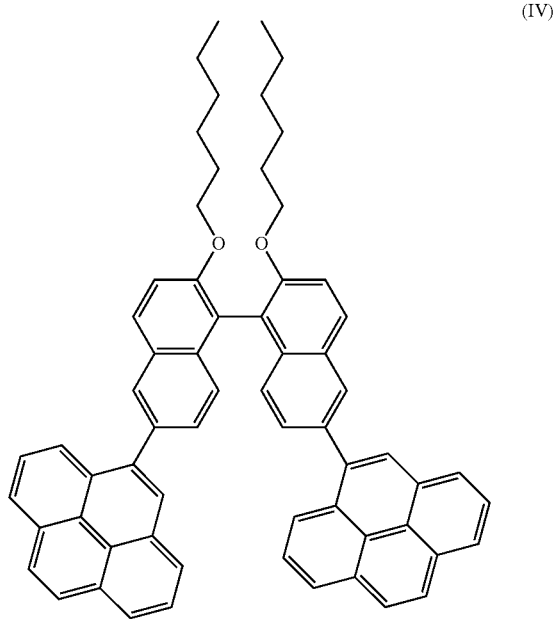

(IV)

A round bottom flask was charged with 6,6'dibromo-2,2'dilaexyloxy-1,1'binaphthyl (895 mg, 1.46 mmol), 1-pyrene boronic ester (1.2 g, 3.66 mmol, 2.5 equivs), sodium bicarbonate (845.3 mg, 7.31 mmol and $Pds(PPh_3)_4$ (84.5 mg, 0.073 mmol, 0.05 equivs). The mixture was evacuated and refilled with Argon three times and dissolved in Toluene/THF/water (3:3:1). The solution was degassed three times and the mixture heated under Argon at 86° C. for 48 hrs. After heating, the solution was cooled down, the solvent evaporated, water was added and the aqueous phase was extracted with chloroform three times. The combined organic phases were washed with brine, dried, evaporated and concentrated under vacuum to afford the crude product. The resulting solid was purified by flash column chromatography on silica gel (hexanes 75%, chloroform 25%) to afford the compound of formula (IV) (424 mg, 35%). The compound of formula (IV) was subsequently purified by sublimation (sublimation temperature: 280° C., 0.07 Pa). Exact mass FAB (M+) calcd for $C_{64}H_{54}O_2$ 854.41, found: 854.41. 1H NMR (400 MHz $CDCl_3$): δ 8.02-8.32 (m, 40H), 7.48-7.62 (m, 8H), 7.25 (m, 8H), 7.45 (m, 12H), 4.11 (m, 4H), 1.55 (m, 4H), 1.13 (m, 12H), 0.78 (t, J=7.2 Hz, 6H), 13C NMR (100 MHz, $CDCl_3$): δ 155.1, 138.2, 136.3, 133.6, 131.7, 131.2, 130.6, 129.58, 129.55, 129.5, 129.4, 128.8 127.6, 127.5, 126.1, 125.75, 125.71, 125.2, 124.7, 124.8, 120.8, 116.4, 70.1, 31.6, 29.6, 25.6, 22.7, 14.2.

DSC measurements on the compound of formula (IV) (4 mg; Temp: 10 deg/min) showed a glass transition at 92.0° C.

Cyclic voltametry measurements for the compound of formula (IV) (1 mM compound in 0.1 M tetrabutylammonium perchlorate (TBAP) in CH2C12; WE: glassy carbon, CE: Pt, RE: Ag): The redox potentials of the compound of formula (IV) were determined with respect to the ferrocene/ferrocenium redox couple ($E_{1/2}$(Fc/Fc+)=0.41 V vs. SCE from a methylene dichloride solution (1 mM), the scan rate was 100 mv/s. Irreversible oxidation and reduction potentials at +1.24 V (vs. SCE) and −2.27 V (vs. SCE) were observed.

EXAMPLE 3

Figure 1B:
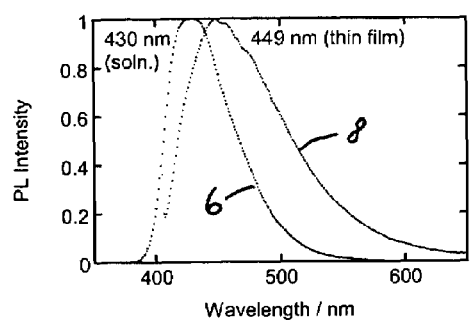
FIG. 1B is a graph showing the normalized PL of a binaphtyl compound.
Figure 1C:
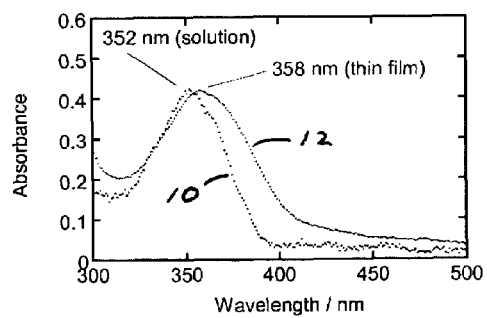
FIG. 1C is a graph showing the absorption of a binaphtyl compound in chloroform.
Figure 1D:
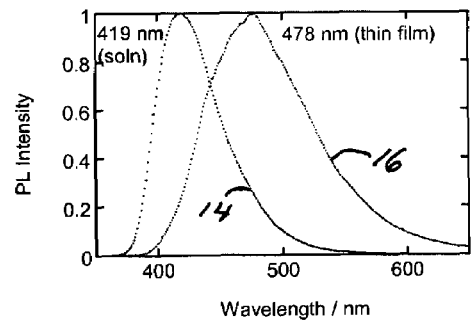
FIG. 1D is a graph showing the normalized PL of a binaphtyl compound.

This example provides a characterization of absorption and emission in solution and thin films of the compound of formula (III) or the compound of formula (IV). The PL, and absorption in solution were measured from chloroform solutions ($10^{-6}$ and $4 \times 10^{-6}$ M respectively). The thin films were prepared by vacuum evaporation. The results obtained are summarized in FIG. 1. In FIG. 1A, the absorption of the compound of formula (III) is shown in chloroform solution 2 and in the solid state 4. In FIG. 1B, the normalized PL of the compound of formula (III) is shown in solution 6 and in thin film 8. In FIG. 1C, the absorption of the compound of formula (IV) is shown in chloroform solution 10 and in the solid state 12. In FIG. 1D, the normalized PL of the compound of formula (IV) is shown in solution 14 and in thin film 16. The compound of formula (III) in solution gave a blue emission ($\lambda_{PL}$ at 430 nm) under UV excitation at 351 nm. The quantum efficiency was 0.89. The compound of formula (IV) in solution also gave a blue emission ($\lambda_{PL}$ at 419 nm) under UV excitation at 370 nm. The quantum efficiency was 0.60. There is almost no change in the absorption in solution and from thin films for the compound of formula (III). However, there was a small red shift (FIG. 1B) in the PL in the thin film compared to solution, and also a broadening of the PL spectrum. In the case of the compound of formula (IV), as shown in FIG. 1D, the spectrum of the compound of formula (IV) thin film (478 nm) is substantially red-shifted, compared to that in solution (419 μm). Absorption spectra are nearly identical (FIG. 1C). This red shift indicates excimer formation or other strong chromophore-chromophore interactions in the solid state.

EXAMPLE 4

This example demonstrates the fabrication of electroluminescent devices using blue emitting binaphthol compounds.

The devices were fabricated by vacuum evaporation of the organic layers (CuPc/α-NPD/EML/SAlq/$Alq_3$) on glass/ITO substrate at about $10^{-6}$ Torr in the same chamber without breaking vacuum. The ITO layer on glass substrate was 120 nm thick, and a stripe pattern with a 2-mm wide ITO layer was etched by photolithographic techniques. The patterned ITO glass was previously ultrasonically cleaned using a detergent, rinsed in water and finished with UV-ozone method. The rates of deposition of the organic layers was between 1.0 and 2.3

Figure 2:
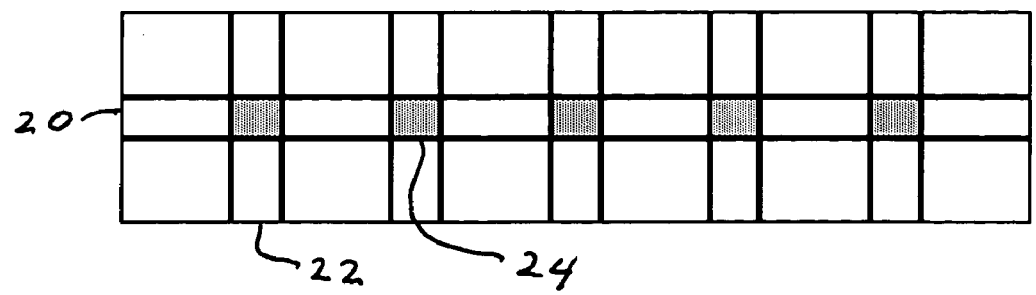
FIG. 2 is a drawing of a stripe pattern etched by photolithographic techniques.

Å/s and the temperatures of deposition were within a range of 206-304° C., depending on the layer. The cathode was deposited in another chamber with a metal shadow mask that defines a 2-mm stripe cathode pattern perpendicular to the ITO anode stripe 20. FIG. 2 is a top view of the device showing the 2-mm wide anode stripe 20 and a deposited 2-mm wide cathode stripe 22. A resulting 2 mm×2 mm emissive area 24 is also shown. The device obtained was encapsulated using a photosensitive resin.

A sketch of a device architecture is shown in FIG. 3. The layers on top of the glass substrate 30 and the ITO layer 31 of 160 nm include a CuPc layer 32 of 10 nm, an α-NPD layer 33 of 60 nm, an emission layer 34 of 30 nm, a SAlq layer 35 of 10 nm, an Alq$_3$ layer 36 of 35 nm, and the cathode 37 having a 0.5 nm layer of LiF and an 80 nm layer of Al.

The hole injection layer contained CuPc (V), and the hole transport layer contained α-NPD (VI).

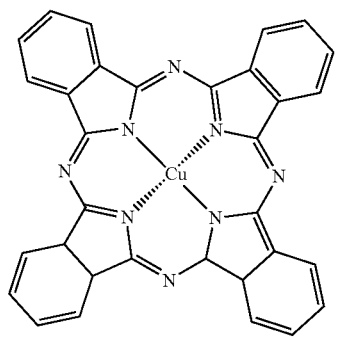

(V)

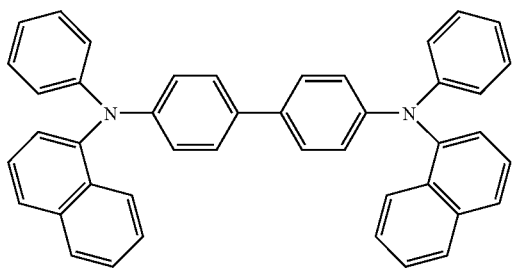

(VI)

The emission layer contained CBP (VII).

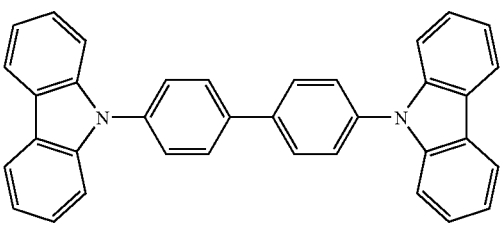

(VII)

The hole blocking layer contained SAlq (VIII), and the electron transport layer contained Alq3 (IX).

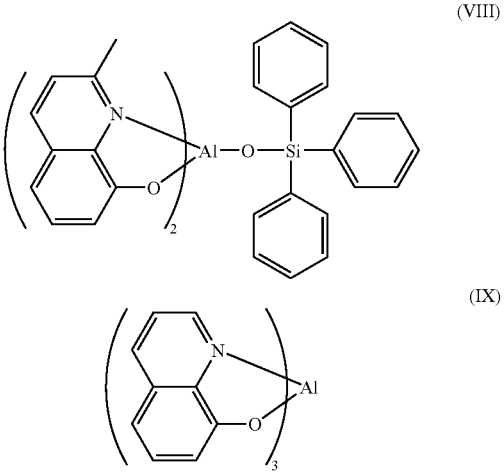

(VIII)

(IX)

EXAMPLE 5

Examples 5-8 provide an evaluation of electro-optical properties of different device architectures. Luminance (L), Voltage (V), Current density (J) were evaluated by assessing the following parameters:

| | |
|---|---|
| $V_{th}$: | threshold voltage (voltage at 1 cd/m$^2$) |
| $L_{max}$: | luminance at 250 mA/cm$^2$ |
| $\eta_{100}$: | efficiency at 100 cd/m$^2$ |
| V100: | voltage at 100 cd/m$^2$ |
| $L/J_{100}$: | efficiency at 100 cd/m$^2$ |

Figure 4A:
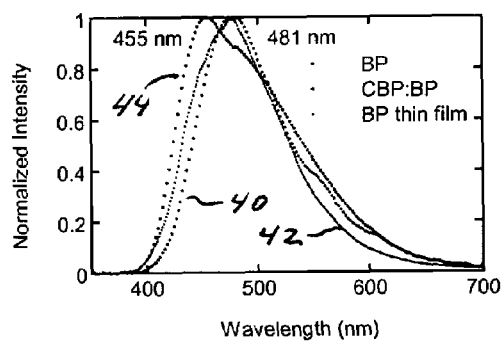
FIG. 4A shows the EL and PL spectra for a binaphtyl compound.
Figure 4B:
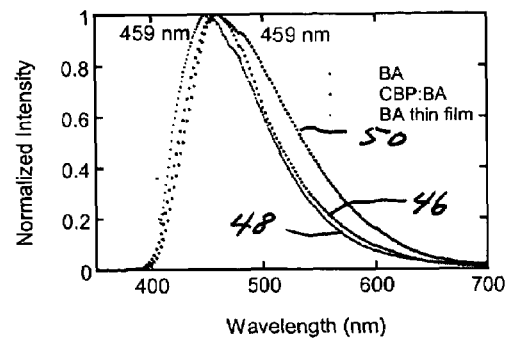
FIG. 4B shows the EL and PL spectra for a binaphtyl compound.
Figure 5A:
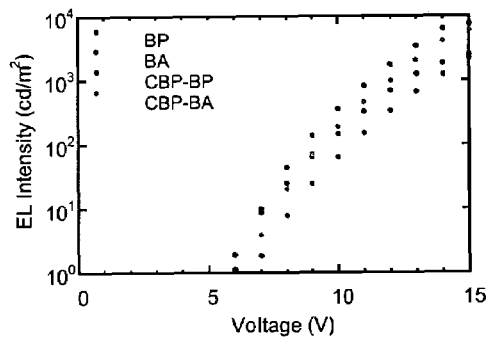
FIG. 5A shows the EL intensity-voltage curves for devices incorporating the binaphtyl compounds of the present invention.
Figure 5B:
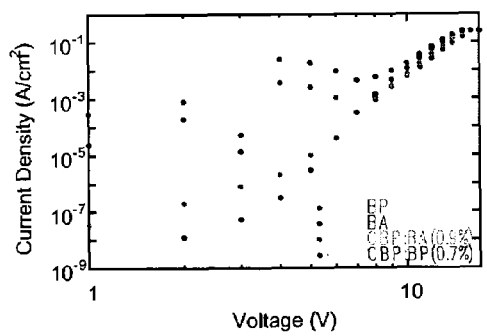
FIG. 5B shows the current density-voltage curves for devices incorporating the binaphtyl compounds of the present invention.

EL spectra of the devices were measured using a multi-channel photodiode array system (MCPD-2000 Otsuka Electrics). The EL (electroluminescence) and PL (photoluminescence) spectra corresponding to the devices of examples 5 to 8 are shown in FIGS. 4A and 4B. FIGS. 5A and 5B show the EL intensity-Voltage and Current density-Voltage curves, respectively, for the devices of examples 5 to 8; In FIGS. 4 and 5, BP refers to the compound of formula (IV) and BA refers to the compound of formula (III).

Devices with the configuration of ITO(160 nm)/CuPc(10 nm)/α-NPD(60 nm)/the compound of formula (IV) (21 nm)/SAlq(10 nm)/Alq$_3$(35 nm)/LiF(0.3 nm)/Al(80 nm) were fabricated, where the compound of formula (IV) refers to the binaphthol electroluminescent material. FIG. 4A shows the EL spectra 40 for the compound of formula (IV) and the PL spectra 42 for the compound of formula (IV) in thin film. The EL spectrum 40 showed a maximum emission at 481 nm, which is identical to the maximum photoluminescence (PL) in the solid state. The device showed a turn on voltage at $V_{th}$, 6.5 V and a $L_{max}$ at 3336 cd/m$^2$ (FIG. 5A); a quantum efficiency $\eta_{100}$ was measured at 0.33 lm/W (FIG. 5A); and a moderate current luminance efficiency ($L/J_{100}$) of 1.10 cd/A was recorded (FIG. 5B).

EXAMPLE 6

Devices with the configuration of ITO(160 nm)/CuPc(10 nm)/α-NPD(60 nm)/the compound of formula (III) (19 nm)/SAlq(10 nm)/Alq$_3$(35 nm)/LiF(0.3 nm)/Al(80 nm) were fabricated, where the compound of formula (III) refers to the binaphthol electroluminescent material. FIG. 4B shows the EL spectra 46 for the compound of formula (III) and the PL spectra 48 for the compound of formula (III) in thin film. The EL spectrum showed a maximum emission at 459 nm, again similar to the maximum photoluminescence (PL) in the solid state (449 nm). The device showed a turn on voltage at $V_{th}$ 5.5 V and a $L_{max}$ at 2528 cd/m$^2$ (FIG. 5A), the efficiency $\eta_{100}$ measured was 0.24 lm/W (FIG. 5A), and a current luminance efficiency (L/J$_{100}$) of 0.72 cd/A was recorded (FIG. 5B).

EXAMPLE 7

Devices with the configuration of ITO(160 nm)/CuPc(10 nm)/α-NPD(60 nm)/CBP(30 nm)-the compound of formula (IV) (0.7%)/SAlq(10 nm)/Alq$_3$(35 nm)/LiF(0.3 nm)/Al(80 nm) were fabricated, where CBP refers to the host material, and the compound of formula (IV) is the dopant dye electroluminescent material co-evaporated with CBP. The compound CBP has redox potentials of +1.27 V(oxidation, HOMO) and −2.41V(reduction, LUMO). The good HOMO-LUMO match between the compound of formula (IV) and CBP makes the compound of formula (IV) a suitable candidate as a dopant. The device showed a turn on voltage at $V_{th}$, 5.95 V and a high $L_{max}$ at 7681 cd/m$^2$ (FIG. 5A), the efficiency $\eta_{100}$ measured was 1.12 Lm/W (FIG. 5A), and a current luminance efficiency (L/J$_{100}$) of 3.04 cd/A was recorded (FIG. 5B). Referring to FIG. 4A, the EL spectrum 44 showed a maximum blue EL at 455 nn, which is slightly blue shifted relative to the maximum photoluminescence (PL) from in the solid state (481 nm). Also observed was a good position in the chromaticity coordinates (0.20, 0.26). No emission from the host material CBP is observed, therefore the compound of formula (IV) is acting efficiently as a dopant dye for this blue electroluminescent LED.

EXAMPLE 8

Devices with the configuration of ITO(160 nm)/CuPc(10 nm)/a-NPD(60 nm)/CBP(30 nm)-the compound of formula (III) (0.9%)/SAlq(10 nm)/Alq$_3$(35 nm)/LiF(0.3 nm)/Al(80 nm) were fabricated, where CBP refers to the host material, and the compound of formula (III) is the dopant dye electroluminescent material co-evaporated with CBP. The match between the HOMO-LUMO energies of the host and the compound of formula (III) makes it a suitable candidate as a dye in a CBP matrix. The device showed a turn on voltage at $V_{th}$ 6.2 V and a high luminance $L_{max}$ at 7413 cd/M$^2$ (FIG. 5A), the efficiency $\eta_{100}$ measured was 0.83 lm/W (FIG. 5A), and a current luminance efficiency (L/J$_{100}$) of 2.45 cd/A was recorded (FIG. 5B). Referring to FIG. 4B, the EL spectrum 50 showed a maximum emission at 459 nm, the color coordinates (0.19, 0.25) indicate a pure blue emission from the compound of formula (III) only, since no emission from CBP is observed. The binapthol based chromophore, the compound of formula (III), acts as an efficient dopant dye for this blue electroluminescent LED.

EXAMPLE 9

Figure 6A:
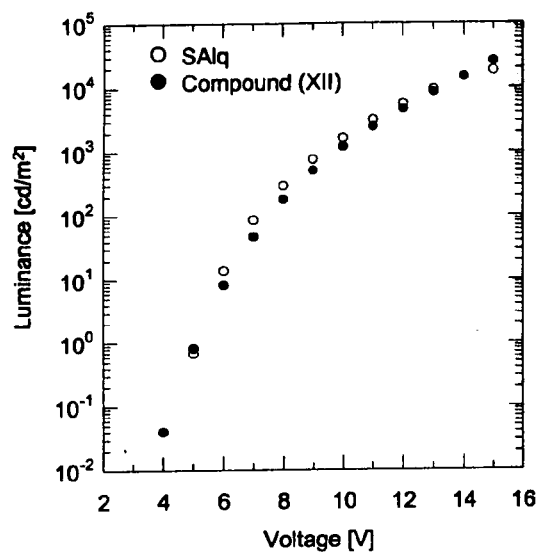
FIG. 6A shows the luminance-voltage curves for devices incorporating the binaphtyl compound as a hole-blocking material.
Figure 6B:
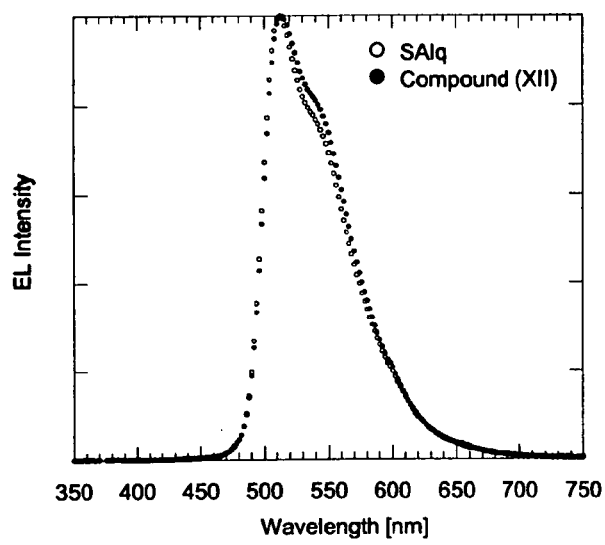
FIG. 6B shows the EL intensity-wavelength curve of the devices of FIG. 6A.
Figure 6C:
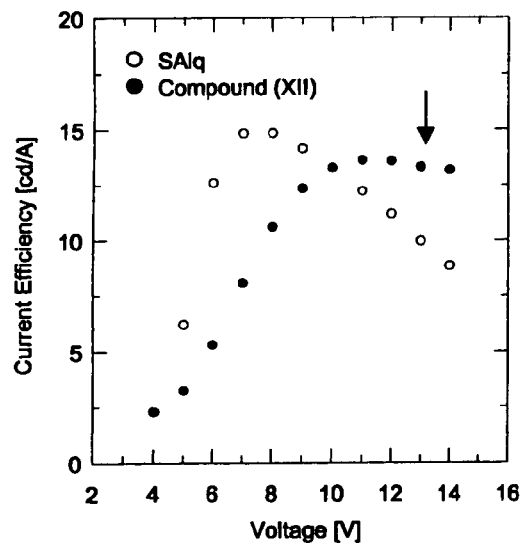
FIG. 6C shows the current efficiency-voltage curve of the devices of FIG. 6A.

Devices with the configuration of ITO(160 nm)/CuPc(25 nm)/PPD(60 nm) of formula (X)/CBP(30 nm) doped with Ir(ppy)3 (5%), formula (XI)/the compound of formula (XII) (10 nm)/Alq$_3$(35 nm)/LiF(0.5 nm)/Al(80 nm) were fabricated, where CBP refers to the host material, and the compound of formula (XII) is the hole-blocking material (see formulas X, XI, and XII below). The IP (Ionization Potential) value of the compound of formula (XII) is 5.64 eV, which makes this layer block holes from the emissive layer effectively. The device showed a turn on voltage at $V_{th}$ 6.2 V and a maximum luminance of 29,270 cd/m$^2$ at V (FIG. 6A), the efficiency $\eta_{100}$ measured was 4.3 lm/W. EL spectra is shown in FIG. 6B where Ir(ppy)3 emission is obtained due to the hole-blocking ability of the compound of formula (XII). Current luminance efficiency of the device is plotted against voltage (FIG. 6C) in comparison with the device having SAlq as a hole-blocking layer, instead of the compound formula (XII). The efficiency degradation of the device in the higher voltage region is significantly relaxed, comparing SAlq hole-blocking layer.

Formula X:

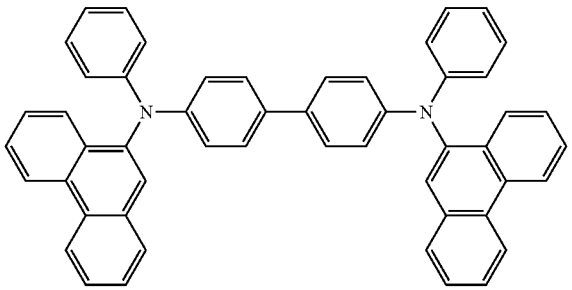

Formula XI:

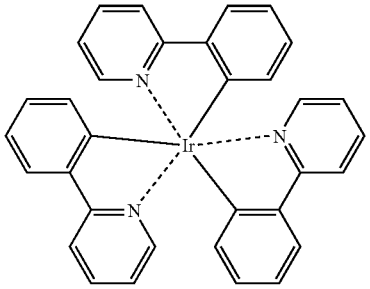

Formula XII:

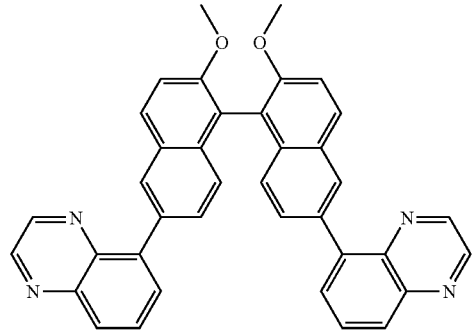

REFERENCES

The following references are hereby incorporated by reference:

Appl. Phys. Lett., Vol. 60, page 2711 (1992); JP-A-5-234681; J. Lumin., Vol. 72-74, page 985 (1997); Chem. Commun., page 2175 (1996); Synth. Metals, Vol. 91, page 209 (1997); JP-A-63-295695; JP-A-4-308688; JP-A-4-145192; Appl. Phys. Lett., vol. 64, p. 1245 (1994); JP-A-4-335087; JP-A-5-70773; JP-A-5-198377; JP-A-59-194393; JP-A-2-216791; P-A-1-245087; JP-A-2-222484; JP-A-1-256584; JP-A-2000-21572; JP-A-11-273867; JP-A-5-159882;

JP-A-5-198380; JP-A-57-51781; JP-A-59-194393; JP-A-6-322362; JP-A-5-198377; JP-A-5-198378; JP-A-5-214332; JP-A-6-172751; JP-A-2-216791; JP-A-1-245087; JP-A-2-222484; JP-A-3-33183; Appl. Phys. Lett., 70, 152, 1997; IEEETrans. Electron. Devices, 44, 1245 (1997); J. H. Burroughs, D. D. C. Bradley, A. R. Brown, R. N. Marks, K. Mackay, R. H. Friend, P. L. Burns and A. B. Holmes, Nature 347, 539 (1990); U.S. Pat. No. 5,189,136; H. Spreitzer, W. Kreuder, H. Becher, H. Schoo, R. Demandt, German Pat. WO 98/27136; European Patent 0544795, WO 9804610A1; H. Becker, H. Spreitzer, Y. Cao, Adv. Mater. 12(1), 42 (2000); D. Braun, G. Gustafssom, D. Mcbranch, J. Appl. Phys. 72, 564 (1992); Chi Zhang, Gang Yu and Yong Cao, U.S. Pat. No. 5,798,170; Ian Park, Yong Cao and C. Y. Yang, J. Appl. Phys. 85(4), 2441 (1999); S. A. VanSlyke; C. H. Chen; C. W. Tang, Appl. Phys. Lett. 1996, 69 2160; Donald Lupo, Josef Salbeck, Hermann Schenk, Thomas Stehlin, Roland Stern, Arno Wolf U.S. Pat. No. 5,480,217; Y. Shirota, J. Mater. Chem. 10, 1 (2000); J. C. Ostrowski, R. A Hudack, M. R. Robinson, S. Wang, G. C. Bazan, Chem. Eur. J, 2001, 7(20), 4500.

What is claimed is:

1. An organic light emitting device comprising an anode and a cathode, and an emissive layer between the anode and cathode, the device including a hole-blocking layer between the emissive layer and the cathode comprising a binaphthyl compound of the formula:

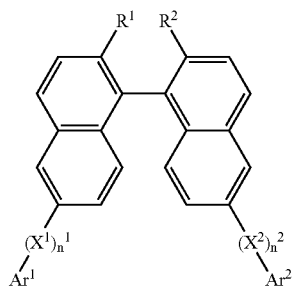

wherein each $Ar^1$ and $Ar^2$ is independently a substituted or non-substituted polycyclic aromatic hydrocarbon or a substituted or non-substituted aromatic heterocycle, each $X^1$ and $X^2$ is independently a substituted or non-substituted aromatic hydrocarbon, each $n^1$ and $n^2$ is independently 0 or 1, each $R^1$ and $R^2$ is independently a hydroxyl group, a substituted or non-substituted alkyl group, or a substituted or non-substituted alkoxy group, wherein $R^1$ and $R^2$ can be bound to each other to form a ring structure wherein the ring structure can have substituent groups, and wherein the compound's binaphthyl framework can be independently substituted by a halogen, a hydroxyl group, or a substituted or non-substituted alkyl, alkenyl, alkoxy or alkoxycarbonyl group at any position except those occupied by $(X^1)n^1Ar^1$, $(X^2)n^2Ar^2$, $R^1$ and $R^2$;

in which the hole-blocking layer between the emissive layer and the cathode comprises a compound of the formula:

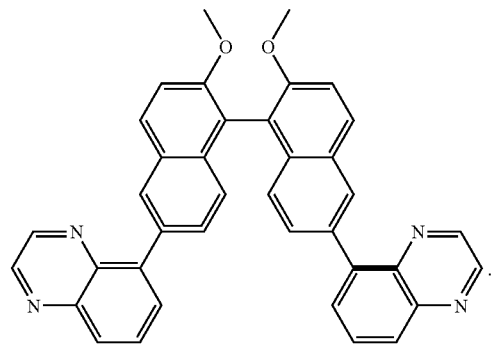

2. A binaphthyl compound of the formula

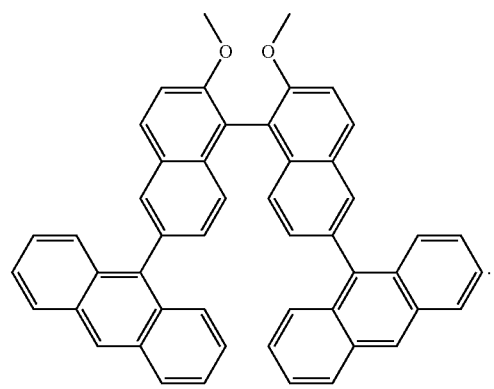

3. A binaphthyl compound of the formula

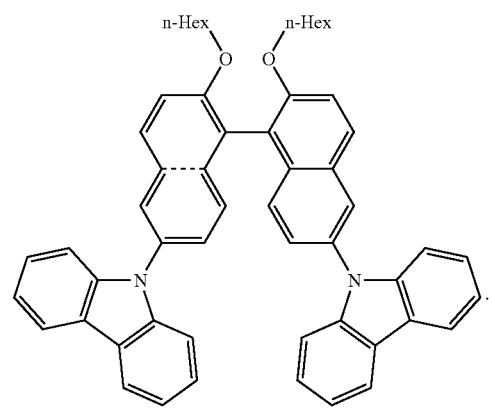

4. An organic light emitting device comprising an anode and a cathode, and an emissive layer between the anode and cathode, the device including a hole-blocking layer between the emissive layer and the cathode comprising a binaphthyl compound of the formula:

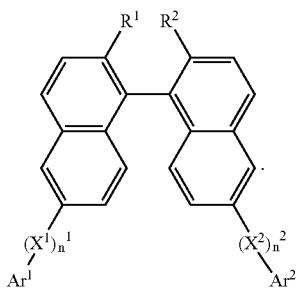

wherein each $Ar^1$ and $Ar^2$ is independently a substituted or non-substituted polycyclic aromatic hydrocarbon or a substituted or non-substituted aromatic heterocycle, each $X^1$ and $X^2$ is independently a substituted or non-substituted aromatic hydrocarbon, each $n^1$ and $n^2$ is independently 0 or 1, each $R^1$ and $R^2$ is independently a hydroxyl group, a substituted or non-substituted alkyl group, or a substituted or non-substituted alkoxy group, wherein $R^1$ and $R^2$ can be bound to each other to form a ring structure wherein the ring structure can have substituent groups, and wherein the compound's binaphthyl framework can be independently substituted by a halogen, a hydroxyl group, or a substituted or non-substituted alkyl, alkenyl, alkoxy or alkoxycarbonyl group at any position except those occupied by $(X^1)n^1Ar^1$, $(X^2)n^2Ar^2$, $R^1$ and $R^2$, in which the hole-blocking layer between the emissive layer and the cathode comprises a compound of the formula:

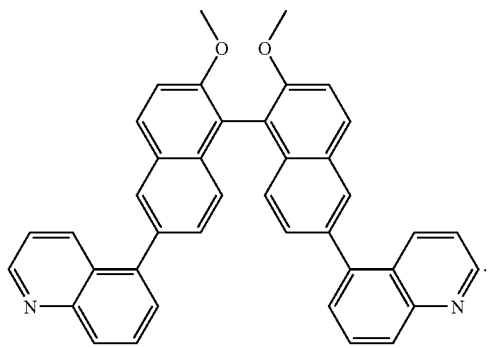

* * * * *